US011559396B2

(12) United States Patent
Pasquino et al.

(10) Patent No.: US 11,559,396 B2
(45) Date of Patent: Jan. 24, 2023

(54) TRANSCATHETER VALVE PROSTHESIS FOR BLOOD VESSEL

(71) Applicant: AorticLab srl, Colleretto Giacosa (IT)

(72) Inventors: Enrico Pasquino, Savigny (CH); Francesco Bonetti, Chieri (IT); Stefano Osta, Saluggia (IT); Franco Osta, Mombello Monferrato (IT)

(73) Assignee: AorticLab srl, Colleretto Giacosa (IT)

( * ) Notice: Subject to any disclaimer, the term of this patent is extended or adjusted under 35 U.S.C. 154(b) by 55 days.

(21) Appl. No.: 16/610,540

(22) PCT Filed: Apr. 23, 2018

(86) PCT No.: PCT/IB2018/052807
§ 371 (c)(1),
(2) Date: Nov. 4, 2019

(87) PCT Pub. No.: WO2018/211344
PCT Pub. Date: Nov. 22, 2018

(65) Prior Publication Data
US 2020/0069421 A1      Mar. 5, 2020

(30) Foreign Application Priority Data

May 17, 2017   (EP) .................................... 17171583

(51) Int. Cl.
*A61F 2/24*       (2006.01)
*A61B 17/34*    (2006.01)
(Continued)

(52) U.S. Cl.
CPC ........ *A61F 2/2427* (2013.01); *A61B 17/3423* (2013.01); *A61F 2/013* (2013.01);
(Continued)

(58) Field of Classification Search
CPC ........ A61F 2/011; A61F 2/013; A61F 2/2427; A61F 2/2436; A61F 2250/0059; A61B 2017/3425
See application file for complete search history.

(56) References Cited

U.S. PATENT DOCUMENTS 7,749,245 B2    7/2010   Cohn et al.
10,213,227 B2   2/2019   Pain et al.
(Continued)

FOREIGN PATENT DOCUMENTS

JP    2006507862    3/2006
JP    2014519370    8/2014
(Continued)

OTHER PUBLICATIONS

International Search Report (ISR) for PCT/IB2018/052807 dated Jun. 27, 2018.
(Continued)

*Primary Examiner* — Martin T Ton
(74) *Attorney, Agent, or Firm* — Nixon & Vanderhye P.C.

(57) ABSTRACT

A transcatheter temporary valve prosthesis for blood vessel comprising an expandable support structure (5"), a valve (7), a filter (12) and a conveyor (6); said support structure (5") forming a tubular shape when expanded, with a distal and a proximal end, said valve (7) being located at said distal end and said conveyor (6) extending within said support structure (5), from said proximal to said distal end and including a central passage that is adapted to act as an introducer for other devices.

16 Claims, 36 Drawing Sheets

(51) Int. Cl.
*A61F 2/01* (2006.01)
*A61B 17/00* (2006.01)
(52) U.S. Cl.
CPC .. *A61F 2/2418* (2013.01); *A61B 2017/00243* (2013.01); *A61B 2017/3425* (2013.01); *A61F 2250/001* (2013.01); *A61F 2250/0059* (2013.01)

(56) References Cited

U.S. PATENT DOCUMENTS

| | | | |
|---|---|---|---|
| 10,568,729 B2 | 2/2020 | Pain et al. | |
| 2002/0095116 A1* | 7/2002 | Strecter | A61F 2/013 604/96.01 |
| 2004/0060563 A1* | 4/2004 | Rapacki | A61B 17/12022 128/207.14 |
| 2005/0015112 A1* | 1/2005 | Cohn | A61F 2/2412 606/200 |
| 2007/0067021 A1* | 3/2007 | Haverkost | A61F 2/2418 623/1.24 |
| 2008/0269877 A1* | 10/2008 | Jenson | A61F 2/243 623/2.11 |
| 2009/0088836 A1* | 4/2009 | Bishop | A61F 2/2418 623/2.1 |
| 2012/0035721 A1* | 2/2012 | Vesely | A61F 2/2412 623/2.36 |
| 2014/0194920 A1 | 7/2014 | Krahbichler | |
| 2015/0066075 A1* | 3/2015 | Russell | A47C 19/02 606/200 |
| 2015/0202038 A1* | 7/2015 | Krahbichler | A61F 2/011 606/200 |
| 2015/0342602 A1* | 12/2015 | Jimenez | A61B 17/3421 606/215 |
| 2015/0342717 A1* | 12/2015 | O'Donnell | A61F 2/2412 623/2.11 |
| 2020/0197033 A1 | 6/2020 | Pasquino et al. | |

FOREIGN PATENT DOCUMENTS

| | | |
|---|---|---|
| WO | WO 2000/044313 | 8/2000 |
| WO | WO 2004043293 | 5/2004 |
| WO | WO 2015/184450 | 12/2015 |
| WO | WO 2015185870 | 12/2015 |
| WO | WO 2020151996 | 7/2020 |
| WO | WO 2020201524 | 10/2020 |

OTHER PUBLICATIONS

Written Opinion of the International Search Authority (WO) for PCT/IB2018/052807 dated Jun. 27, 2018.
Japanese Office Action dated Mar. 8, 2022 for Application No. JP 2020-514782 (translation).

* cited by examiner

TRANSCATHETER VALVE PROSTHESIS FOR BLOOD VESSEL

CROSS REFERENCE TO RELATED APPLICATIONS

The present application is a United States national stage application of International patent application PCT/IB2018/052807 filed on Apr. 23, 2018 designating the United States, and claims foreign priority to European patent application EP 17171583.2 filed on May 17, 2017, the contents of both documents being herewith incorporated by reference in their entirety.

FIELD OF INVENTION

The present invention relates to an expandable prosthetic valve that is designed to be positioned within a blood vessel, during the repair of replacement of a native valve, for instance an aortic valve.

BACKGROUND

The clinical complications related to the implant of a transcatheter heart valve prosthesis (TAVI) are mainly related to the fact that it overlapps the diseased native valve. The heavy presence of tissue calcifications, involving the valve apparatus and the surrounding tissues, influences the correct deployment of the prosthesis creating the conditions for embolic episodes.

The different types of clinical complications, associated with the TAVIs implant, are therefore mainly related to the dystrophic calcifications of the native valve and to the inhomogeneous deployment of the valve prosthesis, and are:
  The occurrence of moderate-severe peri-valvular leaks (grade II)
  The occurrence of embolic events (blood clots and fibrous or calcific emboli The occurrence of moderate-severe peri-valvular leaks (PVL) after transcatheter aortic valve prostheses implantation is at least 10% with a peak of mortality around one year for this particular patients' subgroup.

The clinical data, suitable for the second generation of transcatheter heart valves, are substantially better than those of the first generation for what concerns the PVL. In fact the occurrence of moderate PVLs dropped to 3.4%, but different authors documented higher percentages of PVL complications in patients with "high calcium scored valves".

The coronary occlusion is a kind of clinical complication generated by two different causes, namely the mechanical occlusion of the coronary ostia is induced by the aortic valve native leaflets or the embolization of calcium debris during a TAVI implant procedure. Despite the occurrence of this clinical complication is only 1% of the TAVI implants it is letal in 50% of the cases even with a delay of few days after the implant procedure. The extension of TAVI implants to the intermediate risk patients is further increasing of serious events to a younger patient population.

The mechanical occlusion of the coronary ostia can occur because the TAVI, during its deployment, is pushing outward the calcified native leaflet creating an obstruction of coronary ostia. The same condition can occur when a TAVI is implanted over a degenerated bioprosthesis. In particular with some bioprostheses, such as the "stentless" ones, the risk coronary ostia obstruction is more frequent when a TAVI is implanted.

The procedural embolic events, so called "macro-embolic cerebral events", are occurring during a TAVI implant procedure (during predilation, implant or postdilation) and are mainly related to the embolization of macro debris of calcium of fibroelatic particles usually targeting the brain (strokes), the coronary arteries or the peripheral organs. However the strokes are the most frightful clinical events occurring, nowadays, at a rate of 2.7% against a rate of 3.3% of the previous generations of TAVIs. This reduction of strokes is related to the minor need of pre- and postdilation during TAVI implant nevertheless this data are unclear since are referring to aortic valves with a mild level of calcification.

The post-procedural micro-embolic cerebral events are documented in at least 8% of the patients submitted to investigation. The high incidence of new cerebral lesions after TAVI warrants for a longer-term evaluation of neurocognitive function.

In this study conducted over a short-term follow-up period of 3 months, no impairment of neurocognitive function was observed clinically, and the majority of lesions (80%) had resolved on 3-month MRI. However, the issue of periprocedural brain embolization and its potential effects on neurocognitive function may portend greater clinical implications once the indication for TAVI is broadened to include younger patients with long life expectancy.

Future research in the field of TAVI should thus be directed at developing strategies to reduce the risk of embolization (eg, less traumatic, smaller-bore catheter systems, improved identification of patients at risk for embolization and a potential use of cerebral protection devices).

In some clinical studies at least 10% of the patients, submitted to TAVI implant, show a neurological damage detectable during psycometric tests. While this occurrence rate can be acceptable in high risk and an old patient population it appears unacceptable in lower-risk younger patients. Several clinical studies are ongoing to better investigate this clinical condition.

Another kind of embolic events are the sub-acute and chronic microembolic events occurring after the immediate post-procedural time. The native aortic calcific valve is rough, with a warty surface, immobilized acting like an atherosclerotic ulcerated plaque. This condition is favouring the formation of microtrombi that later-on embolize towards the brain and other peripheral organs. The native aortic valve left in place as a source of microemboli has been taken in account in several clinical studies that demonstrated their role in the onset of vascular origin dementia. This evidence creates a concern when the TAVI are implanted in younger patients where an acceleration of the vascular dementia could impact in a serious way on the social costs.

In summary the periprocedural clinical complications following a TAVI implant are strongly related to the presence of the heavily calcified aortic valve left in place. It brings, acutely, an occurrence of macro-embolic cerebral events (strokes) and haemodynamic consequences such as the PVLs resulting in a various severity of aortic valve insufficiency. These unsatisfactory clinical outcomes are closely related to an irregular deployment of the transcatheter valve prostheses in concomitance of highly calcified aortic native valves.

The longer term clinical complications are characterized by the cerebral micro-embolizations generated by the native aortic valve leaflets' left in place that become a source of emboli responsible for vascular dementia.

The overall rate of clinical complications in TAVI is ranging between 5% and 12%. This occurrence is most probably underestimated because it does not include patients with highly calcified and biscuspid native valves.

These evidences highlight the importance of protecting the peripheral organs, in particular the brain and the heart, against embolizations occurring during TAVIs procedures.

Nowadays, there are several devices on the market that protect the organs from embolic products, acting as deflectors or anti-embolic filters. In the case of the deflector, the protection system deflects emboli from the brachiocephalic trunk and the left common carotid artery towards the peripheral circulation. In the case of the anti-embolic filters, they actually capture emboli with a mesh.

International patent application WO 2015/185870 discloses a temporary valve prosthesis that is designed to be inserted into the aortic root at the sinotubular junction.

The device comprises a filter that is contained within a valve having a conical shape.

This above cited device provides some improvements with respect to other prior art devices. It however shows some inconvenients, such as a risk of leakage resulting from a blood back flow or the difficulty to insert additional devices through the prosthesis due to catheter dimensional constraints.

SUMMARY OF THE INVENTION

The inconvenients discussed in the previous chapter are solved with the present invention that relates to a device as defined in the claims.

More precisely, the present invention consists of an integrated system providing, at the same time, an antiembolic protection, a valve function as well as a self-centering conveyor for other devices. The conveyor function is suitable for entering and centering transcatheter devices operating on the diseased native valve (devices for mitigation of native leaflet stiffness or partial/full ablation of the native valve) or TAVI or other valves to be implanted. This system can therefore optimize the overall TAVI procedure and it could be very effective in reducing the acute peri-procedural clinical complications that could arise especially in complex procedures.

The device according to the present invention is conceived to be entirely collapsed inside a catheter and introduced in the patient's artery with the aim to reach the aortic arch and to be deployed in place. The device allows to be crossed by different transcatheter devices performing procedures on the native valve while is providing a temporary valve support and protecting the heart, the brain and peripheral organs from any kind of embolizations.

The device can be completely or partially collapsed during the procedure in order to be re-positioned. At the end of the procedure the device is collapsed, retracted inside the shaft and fully retrieved out from the patient.

This device preferably has a valve prosthesis contained inside a shaped support structure that leak-free couples with the aortic wall. A second structure, either internal or distal respect to the support structure acts like an antiembolic filter. A third structure, with a conical or funnel like shape called conveyor, can be either internal or distal respect to the support structure and crosses the inner lumen of the valve prosthesis. It has the function to create a conduit across the device and to facilitate the introduction of several transcatheter devices operating on a diseased aortic valve, and the relevant alignment respect to the valve axis.

In one embodiment the valve prosthesis is anchored to the internal surface of the support structure. In this case the expansion of the external support structure, to get in contact with the aorta's wall, is conditioned by the internal valve prosthesis. Therefore the dimension of the device must be determined with accuracy at the time of the intervention in order to avoid a prosthetic valve insufficiency with a limited efficacy in term of haemodynamic performance and antiembolic protection.

In another group of embodiments the valve prosthesis can be considered independent from the antiembolic filter so that the expansion of the last one, to fit to the aorta's wall, does not interfere with the valve prosthesis function. This embodiment requires that the external support structure and the inner valve prosthesis are connected by a sort of diaphragm. In this way the dimension of the inner valve prosthesis is independent from the diameter change of the external support structure when fitting to the aorta's wall. Several embodiments belong to this group, differing in terms of positioning of the filter and conveyor elements and materials of the support structures, namely with embodiments having the conveyor and/or the filter internal or outside the main support structure and embodiments having all support structures made of self-expanding metallic materials or inflatable structures or hybrid ones.

DETAILED DESCRIPTION OF THE INVENTION

The invention will be better understood below, in association with some illustrated examples.

Numerical References Used in the Figures

1 Guidewire
2 Balloon catheter tip
3 External shaft catheter of the device
3' Internal shaft catheter of the device
4 Device
4' Tethering struts connecting the device to the internal shaft catheter 3'
4" Tethering struts connecting the conveyor 6 and the valve's support stent 14
5 External support structure of the device
5' Anchoring holes to filter mesh
5" Combined internal structure (including elements 6 and 14)
5''' Tethering struts with keyholes connecting the structure 5" (valve' support stent 14 and conveyor 6 combined in a single element) with the external support structure 5
6 Conveyor (integrated in 4 or outside)
6' Internal lumen of conveyor
6" Distal conveyor's tube with a bi-directional normally closed valve
6''' Anchoring holes for a conveyor placed outside the device 4
7 Leaflets of internal valve prosthesis
8 Coronary artery deflectors
9 Epiaortic vessel deflector
10 Mesh mounted on the internal or external surface of the support structure 5 coupling with the aorta's internal surface with antiembolic filter functions
11 Junction ring to the internal shaft catheter 3'
11' Junction ring joining the device with the external convejor 6
12 Antiembolic filter mesh normally mounted on the conveyor 6
13 Junction diaphragm between the external support structure and the internal valve's prosthetic structure 12
14 Valve's support stent 14' Leaflets' anchoring structure
14" Junction pillars between tethering struts 4" and valve's support
15 Prosthetic valve
16 Inflatable structures
17 Mechanism to force open the valve leaflets 7
18 Radiopaque markers

PROCEDURE

Figure 5:
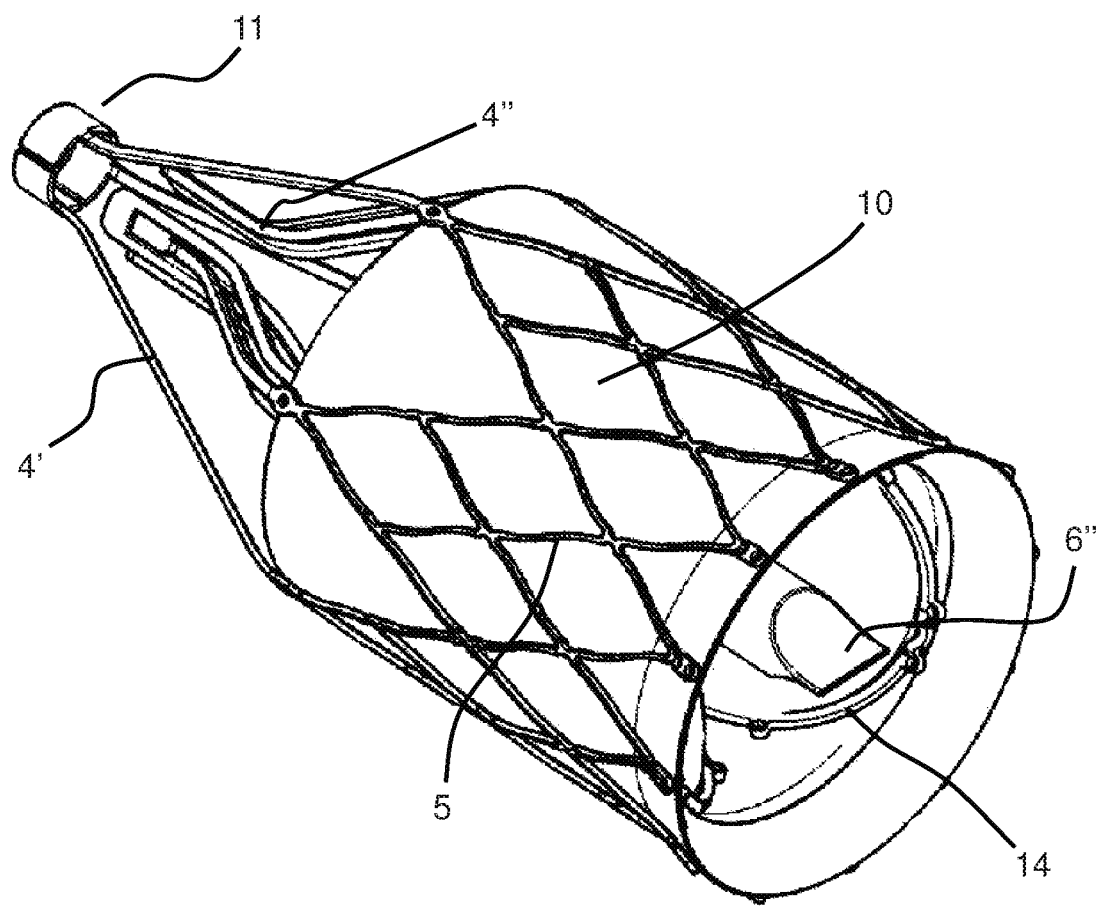
FIG. 5: Hybrid device 4 in deployed configuration (long axis view).

In this chapter the procedure is described with the item description referred to one embodiment that has the valve, filter, and conveyor elements inside an external support structure (see FIG. 5). It is intended that the procedure is also applied with the other embodiments with different item mutual positioning.

Figure 1:
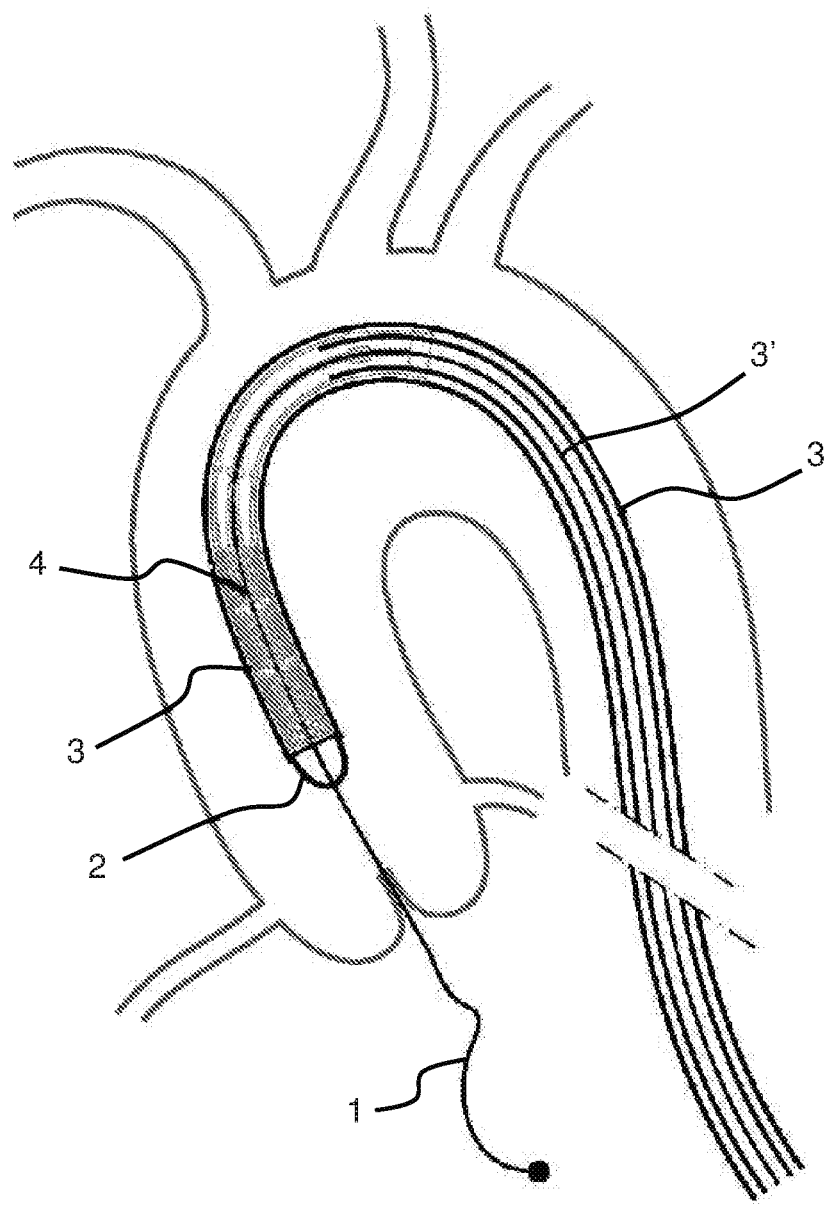
FIG. 1: Device 4 closed inside the shaft 3 and positioned in the aorta at level of the sino-tubular junction.
Figure 2:
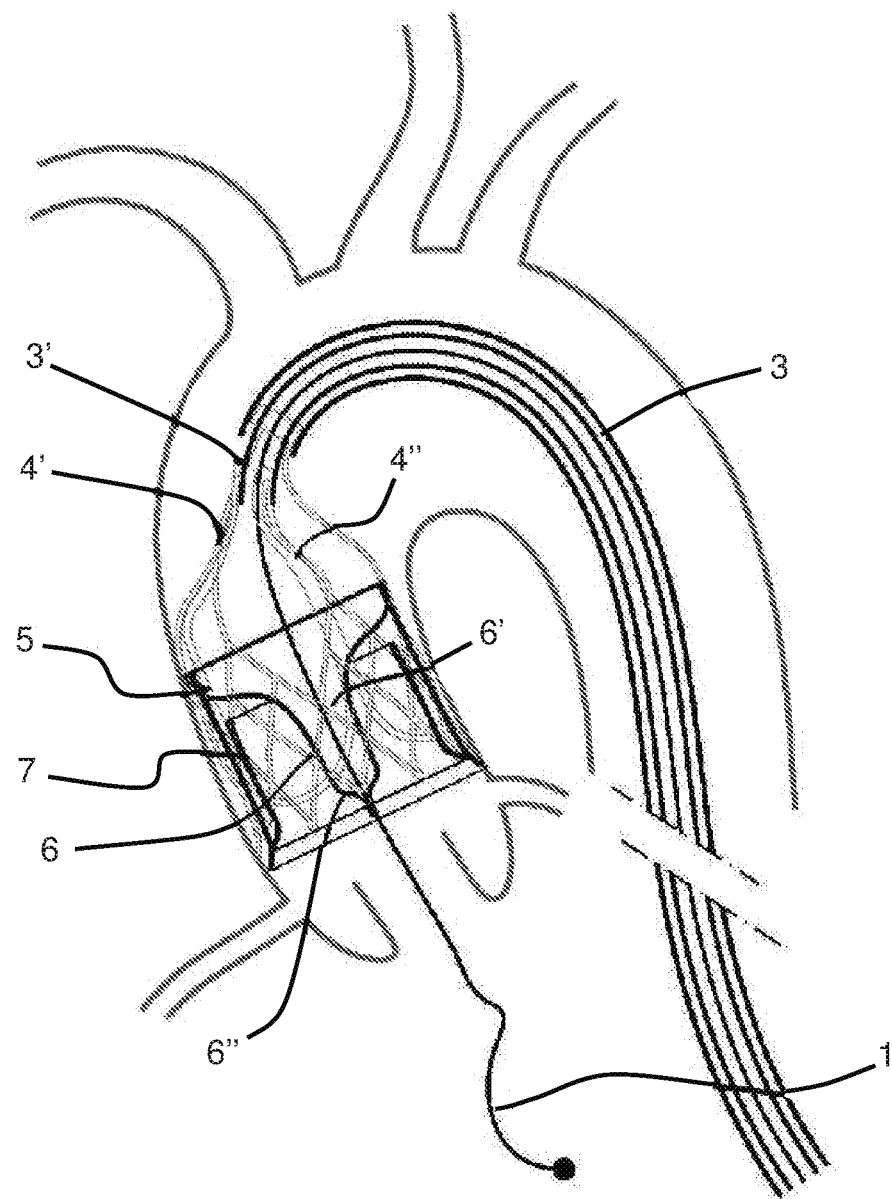
FIG. 2: Device 4 deployed in the ascending aorta, with open prosthetic valve.

The device is collapsed into the external shaft catheter 3 before to introduce it into the arterial vessel (FIG. 1). The distal portion of the external shaft catheter is equipped with a balloon catheter tip 2 deployed across the edge of the external shaft catheter 3. The function of this balloon tip is to avoid any arterial wall damage during the device traveling towards the ascending aorta while ensuring precise positioning being inflated with radiopaque solution. When the device is positioned at level of sino-tubular junction the balloon tip is deflated and retracted outside the patient's body. In FIG. 2 the device is deployed inside the ascending aorta retracting the external shaft catheter 3. When the device is deployed, the external support structures 5 are fitting the aorta's wall in order to convey all blood into the device. The device 4 is connected to the internal shaft catheter 3' by means of struts or theters 4'. Internally, the device has two components sustained by the external support structure 5: the conveyor 6 and the valve prosthesis 15. The conveyor 6 is proximally fixed to the proximal portion of the external support 5 and delimits "like a funnel" a channel 6' inside the device. The role of the conveyor is to allow devices (valvuloplasty balloons or TAVI, etc.) crossing towards the aortic valve. For the specific embodiment described, another function of the conveyor 6 is to support the antiembolic filter. The role of the prosthetic valve, equipped with two, three or more leaflets, is to avoid a massive blood flow regurgitation during interventional procedures on the native aortic valve (e.g. significant perivalvular leakage after valvuloplasty, TAVI implant or in the future, an interventional ablation of the aortic valve). The prosthetic valve 15 can be directly anchored to the distal edge of the external support structure 5 but in the described embodiment it is mounted on an independent valve support and joined to the external support structure 5 by a diaphragm of fabric. The valve function is granted by the coaptation of the leaflets that in closure phase adhere to the distal external surface of the conveyor 6. FIGS. 2 and 2a respectively show the device 4 and the diseased valve respectively in the closed and open positions.

Figure 3:
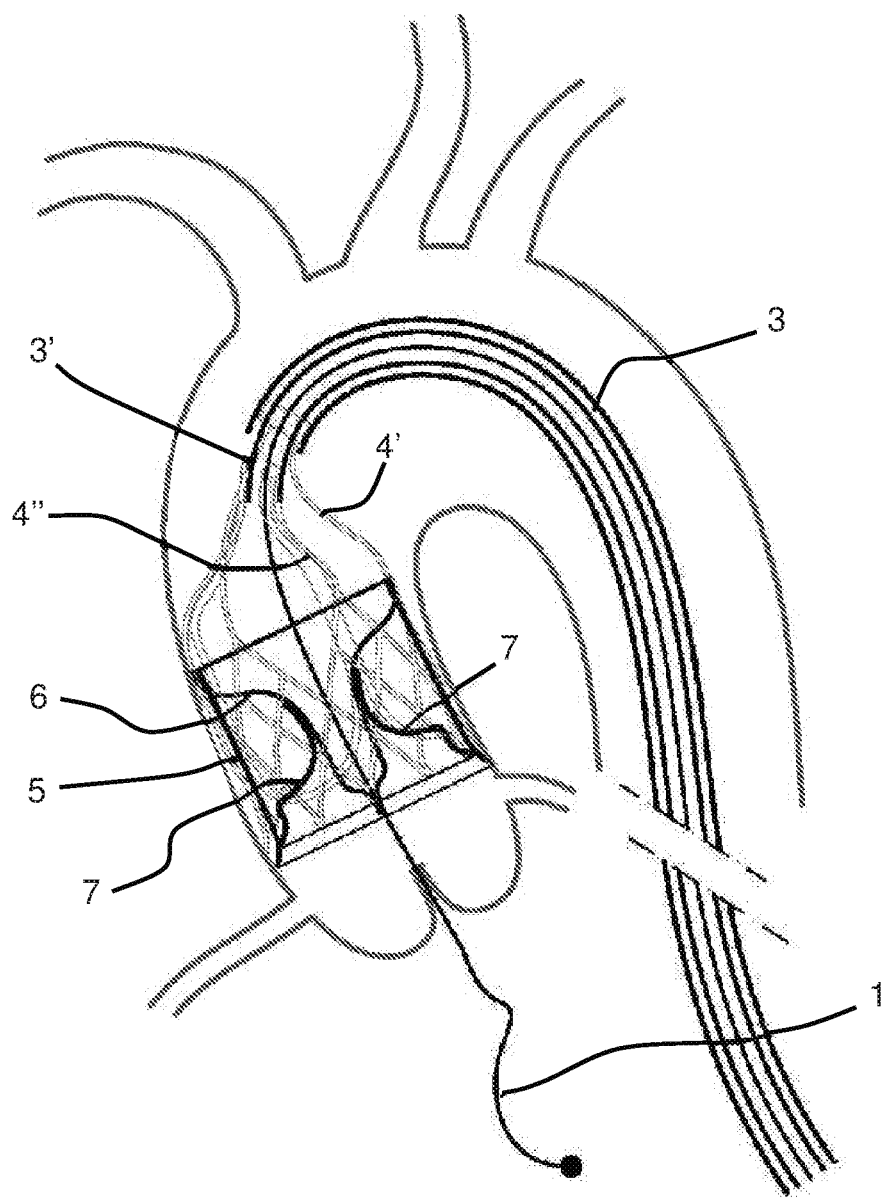
FIG. 3: Device 4 deployed in the ascending aorta, with closed prosthetic valve.
Figure 3A:
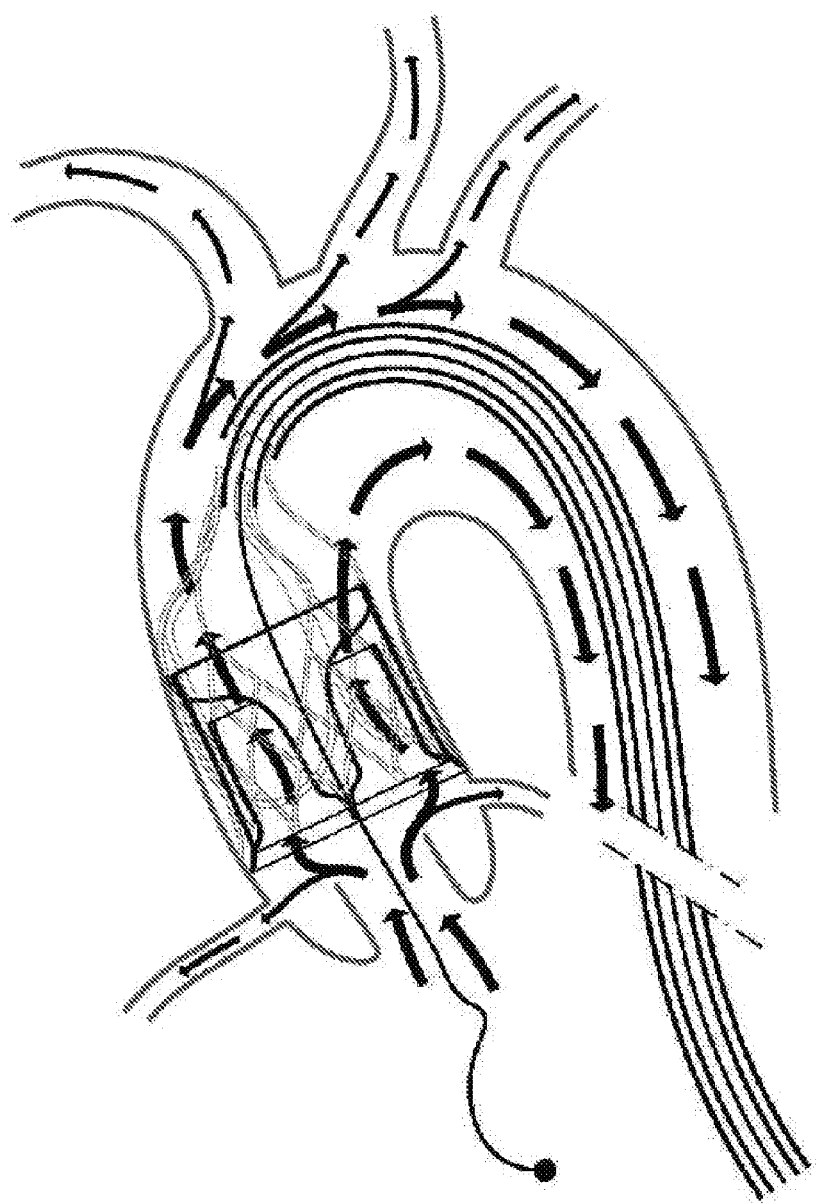
FIG. 3a: Device 4, as in FIG. 3, deployed in the ascending aorta showing the blood flow direction.

In FIG. 3 the device is represented deployed as in FIG. 2 but the device is equipped with an additional feature represented by two coronary artery filters 8 and one epiaortic vessels filter 9. The first one impedes possible debris embolizations into the coronary ostia during an interventional procedure on the aortic valve. This event despite being not very frequent is very often catastrophic. The second one is aimed at avoiding possible residual debris, accidentally not completely captured by the device 4, to embolize towards the brain causing a stroke. This deflector can be deployed, in case of high risk procedures, by further retracting the external shaft catheter 3.

The above mentioned coronary artery and epiaortic vessels protection system can be virtually applied in any of the specific embodiment here-below described.

Figure 4:
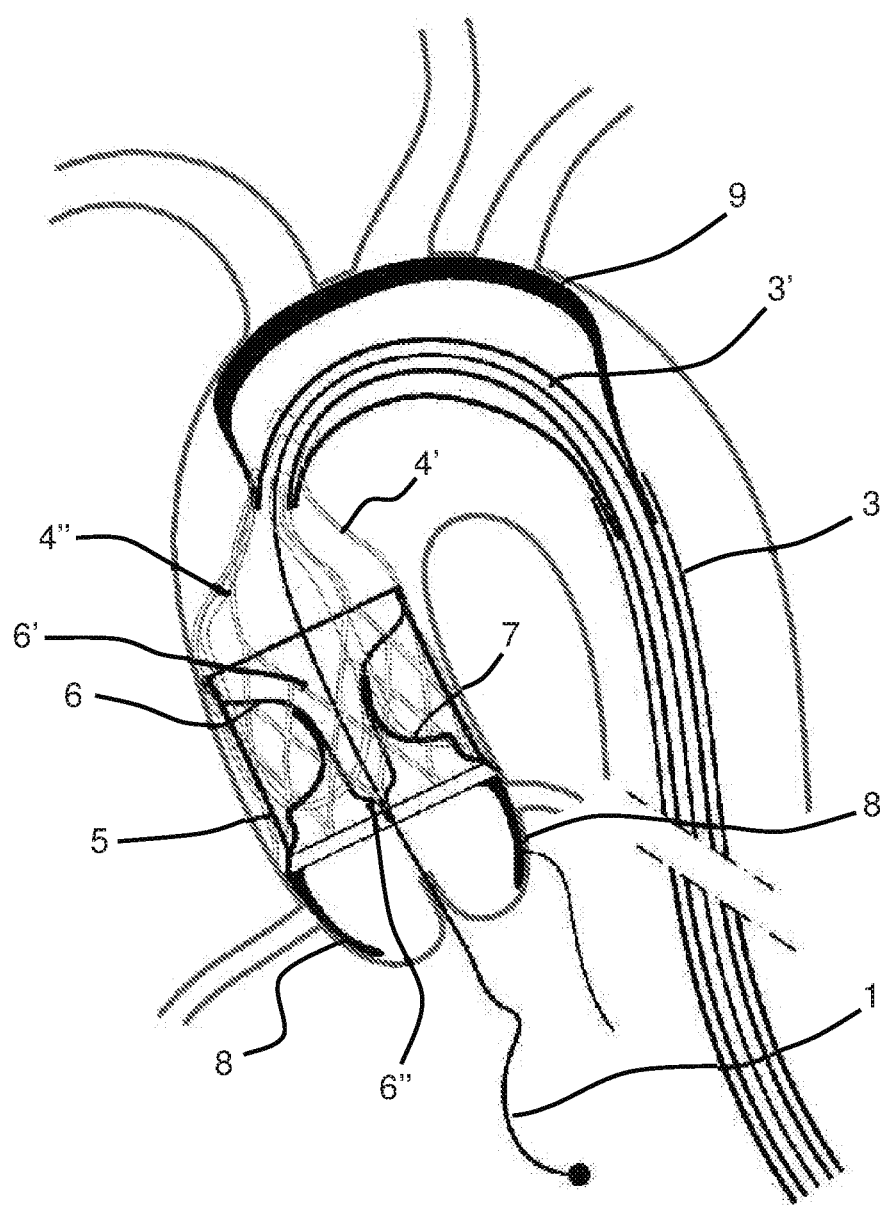
FIG. 4: Device 4 deployed in the ascending aorta with coronary artery deflectors 8 and epiaortic vessels' deflector 9.
Figure 4A:
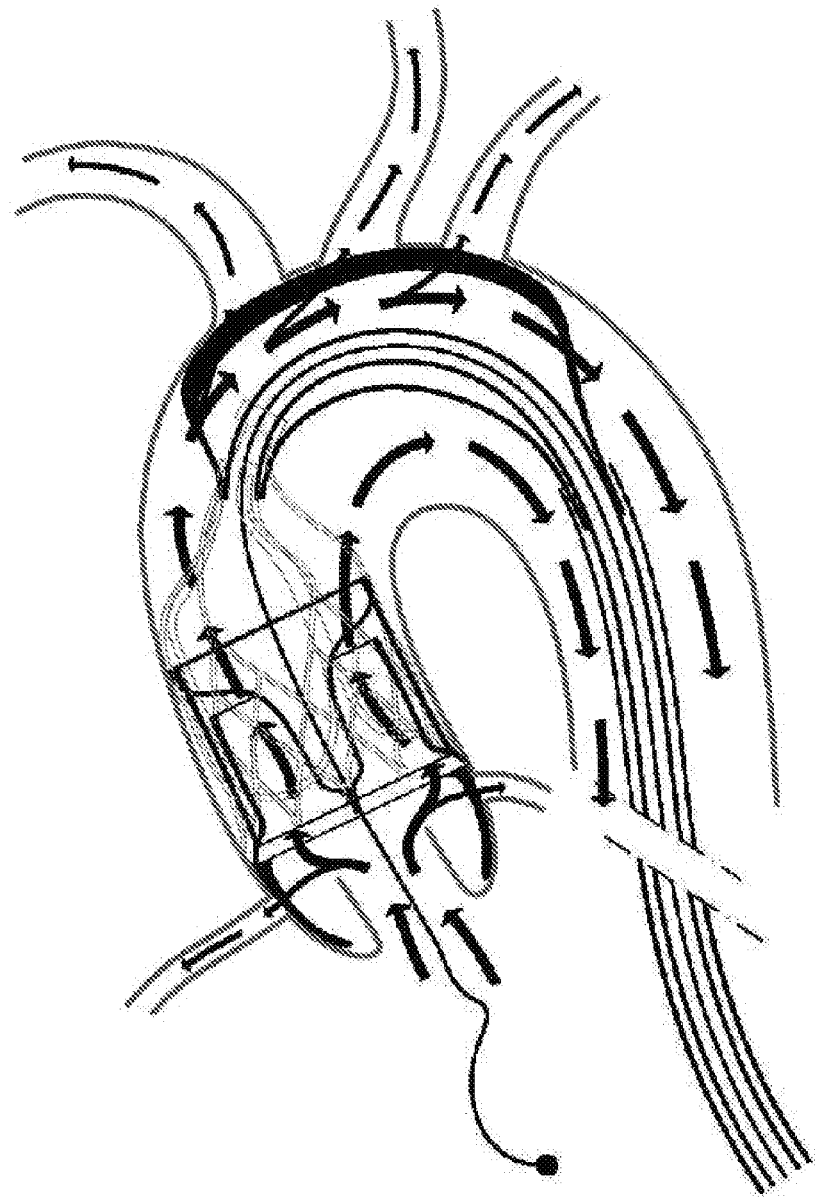
FIG. 4a: Device 4, as in FIG. 4, deployed in the ascending aorta showing the blood flow direction. The deflectors block the emboli but do not impede the blood perfusion.

During the function the blood flow in systole crosses the native aortic valve, opens the valve prosthesis and crosses the antiembolic filter 6. FIG. 4 details the blood flow direction in systole, with the main flow pattern trough the aorta, together with the flow pattern through the epiaortic vessels and a flow trough the coronary artery, granted by a non complete sealing of the coronary ostia by the native valve.

The embolic debris are captured and remain inside the structure in between the conveyor 6 and the external support structure 5.

If needed the device can be left in place for a period in order to allow a stabilization of the patient's haemodynamics and then removed. In this case, a specific mechanism can be used that forces the prosthetic valve open to verify the native valve functionality restoring upon treatment and repeat the treatment if needed. The above mentioned valve opening mechanism can be virtually applied in any of the specific embodiment here-below described.

At the end of the procedure the devices that operated on the aortic native valve are removed out from the internal lumen of the conveyor 6'. The device 4 is completely retrieved by pushing distally the external shaft catheter 3. In this way, the device structures gradually collaps until reaching the distal end of the device safely keeping inside it all captured clots or calcium debris.

The device 4 is conceived to provide an effective antiembolic protection during interventional procedures on the native aortic valve as well as support the blood circulation in case an aortic valve insufficiency is present.

In particular a mild to severe valve insufficiency of the native valve can occur after a balloon valvuloplasty, a suboptimal TAVI implant or a TAVI misimplantation with consequent migration. This last condition can be clinically catastrophic with limited possibility of patient's survival.

In another future condition the device is absolutely necessary. It is the case in which the diseased native aortic valve is removed with an interventional off-pump procedure. In this complex procedure during the dissection of the native valve an antiembolic protection is mandatory and even more important an ancillary aortic valve function is demanded in the meantime a sutureless valve prosthesis is implanted. The device can answer to all these needs.

In a particular embodiment the valve that is integrating in one single device the antiembolic filter and a valve prosthesis could provide the two components detachable.

In the case of interventional ablation of the diseased native aortic valve after its removal the prosthetic valve could be detached from the device 4 and left in place as a permanent sutureless valve prosthesis similar to a TAVI procedure.

DESCRIPTION OF THE DEVICE MAIN ELEMENTS

Valve Prosthesis

The valve allows to temporarily replace the diseased valve during the procedure, while allowing hydrodynamic performances compatible with clinical conditions of patients with aortic stenosis.

Support Structure

The support structure can be either a single element structure 5" or a multielement one. In the first case, it has the functions of coupling with the aorta, support the valve and filter and act as conveyor. In the second case, the external support 5 has the function of coupling with the aorta and support other structures. The valve's support stent 14 has the aim to support the valve leaflets; the conveyor support 6 is here below described. The internal surface of the support 5 (5") is covered by an antiembolic tissue mesh 12 in order to allow a better sealing of the device against the aortic wall but also to impede emboli migration in case of limited contact.

Filter

The filter 12 allows to retain the emboli debris without significantly alter the hydrodynamic characteristics of the valve. In some embodiments, the filter and the conveyor fabric are joined in a unique element.

Conveyor

The conveyor 6 is the introducer element of the TVAF: it makes an easier in situ positioning of specific devices (i.e. TAVI) loaded with external catheter 3, thanks to the geometry of its elements. Typically, a series of elements interconnected: a conical support structure with an antiembolic mesh lining, such as fabrics or membranes, a distal cylindrical expandable tubular part with an impermeable lining and a bi-directional normally closed valve.

In some embodiments, the conveyor 6 and the valve's support stent 14 are joined in a unique element 5".

Internal and External Shaft Catheters

The internal shaft catheter 3' support the device 4, permanently in the default set-up. The internal shaft catheter is protected by the external shaft catheter 3 that has the function to guide the device in position and to allow the deployment/recapture of the device 4.

The present invention is of course not limited to the embodiments and examples discussed in the present document. Therefore the disclosures should not be limited by any particular element hereinafter described.

More into details, as far as concerns the materials: the support structures are here described as made for most of the embodiments by self-expanding metallic materials like nitinol, but also other metallic and non metallic materials with similar characteristics can apply and also non self-expandable structures like polymeric inflatable ones can apply; the filter is described as a polymeric woven fabric, but also non-woven (i.e. membrane with calibrated holes) and or metallic materials with similar characteristics can apply; the valve is described as a polymeric woven fabric coated for ensuring leak-free characteristics, but also non-woven with similar characteristics can apply; the catheters comprises a polymeric tube, but also a metal-reinforced polymeric tube.

As far as concerns the techonologies: the metallic support structures are described as obtained by laser cutting tubes or welded sheets, by woven (i.e. by a plurality strands) and single wire structures; the coupling between the different elements of the device can be either glueing, soldering, welding (i.e. ultrasound), adhering, sewing, and other applicable methods; the valve can be obtained by coating of a fabric, but also other synthetic or natural materials can also apply, such as a polymeric membrane.

As far as concerns the embodiments: in the description, embodiments deemed to be used with femoral access to restore the diseased aortic valve are shown. At the same time, also embodiments with access different from femoral can also apply. A specific embodiment where the valve part can be disloged by the rest of the assembly can apply, in order to be used as a TAVI or a sutureless valve prosthesis. In this case, the valves' leaflets can be manufactured with material different respect to polymeric ones, such as pericardial tissue or other and the valve structure can also have specific retrieval elements.

Moreover, also embodiments to restore other diseased heart valves can apply.

The device can also apply in other technical fields, such as the interventional radiology, as a valved, or not, filter for carotid artery protection as well as a repositionable/recapturable venous valve with antiembolic filter. In this cases specific embodiments and dimension for the different elements to be used amongst the default set-up (valve, filter, conveyor and relevant support structures, catheters) and the expected use (acute, subacute, chronic) will apply.

In terms of dimensions, those related to the specific use will apply, such as the anatomy dimensions of the health and diseased organs to be treated, the access size for the different transcatheter approach, the filter size to protect from the embolization in the coronary and epiaortic arteries.

FIGS. 5 to 11 show one embodiment, hereinbelow referred as hybrid device being the techonology used for manufacturing the self-expandable nitinol structures laser cutting for the external support structure 5 and valve's support stent 14 and braiding or wiring for the conveyor 6.

In this embodiment, the external support structure 5 and the inner valve's support stent 14 are connected by a sort of diaphragm 13, thus ensuring deployment of the inner prosthetic valve 15 independent respect to the external support 5 and antiembolic filter elements. The conveyor 6, which also acts as the filter support, is positioned inside the external structure 5 in order to reduce the overall device length.

In FIG. 5 a long axis view of the device in deployed configuration shows the rings that permanently joints the internal shaft catheter 3' to the external self-expandable support structure 5 and the conveyor 6 and valve's support stent 14 by means of the tethering struts 4' and 4". In FIG. 5 it is also shown the coupling between the external support structure 5 and the internal mesh lining 10, that ensures a leak free contact to the aortic walls.

Figure 6:
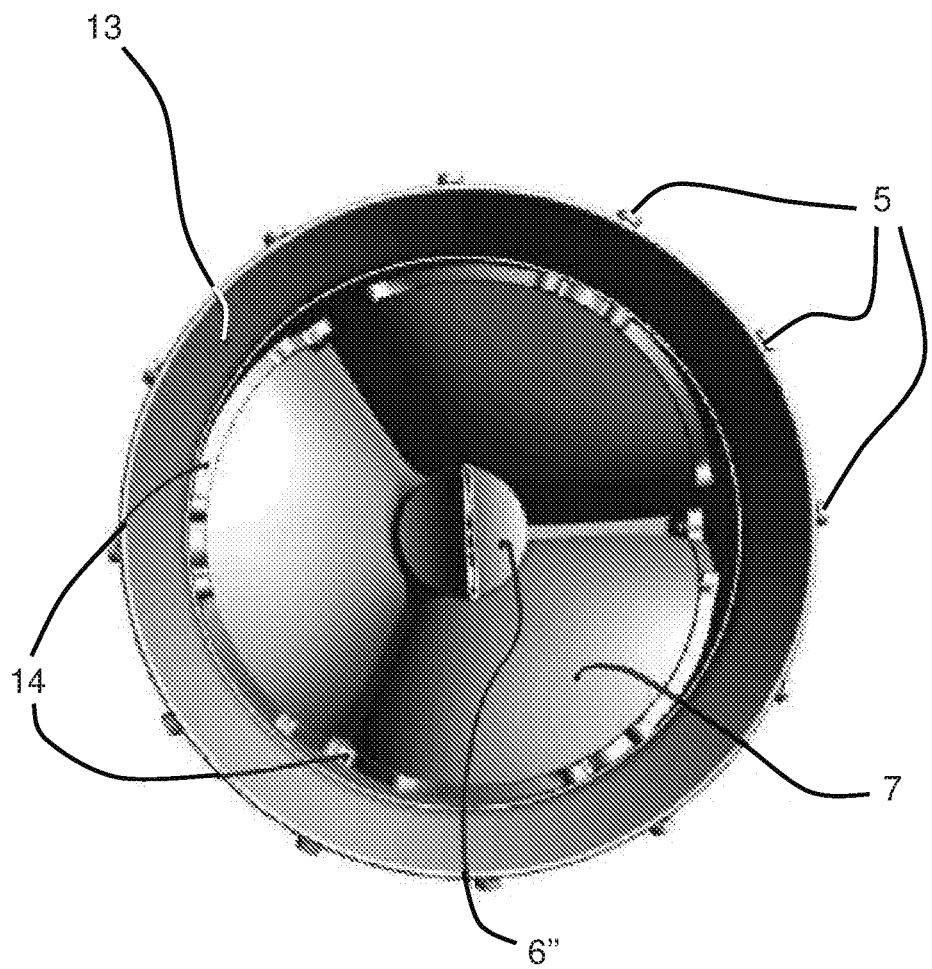
FIG. 6: Hybrid device 4 in deployed configuration (short axis view or ventricular view).

In FIG. 6 a short axis (ventricular) view of the device 4, in a deployed configuration, shows the anchoring holes between the external structure 5 and the mesh 10, that is reverted at the distal side and is joined to the valve prosthesis 15 leaflets 7, these latter covering the external side of the self-expandable material internal valve's support stent 14. The absence of leakage in the diastolic phase is guaranteed by the impermeable mesh of the leaflet elements 7 and of the mesh 10 together with the configuration of the conveyor conduit, which is distally equipped with a bi-directional normally closed valve 6". Both in systole and diastole the valve 6" remains closed, in order to prevent any blood and possible embolic particles leakage; when the transcatheter devices are introduced, the distal conveyor's tube 6" extends in diameter facilitating their introduction maintaining a proper alignment, whilst the valve 6" allows a virtually leak free crossing of the device. The valve 6" can be either directly operated by the delivery system or automatically, remaining strictly closed at the systolic and diastolic differential pressure, but capable to be crossed by the insterted device delivery system, whilst maintaining a leak free coupling.

Figure 7:
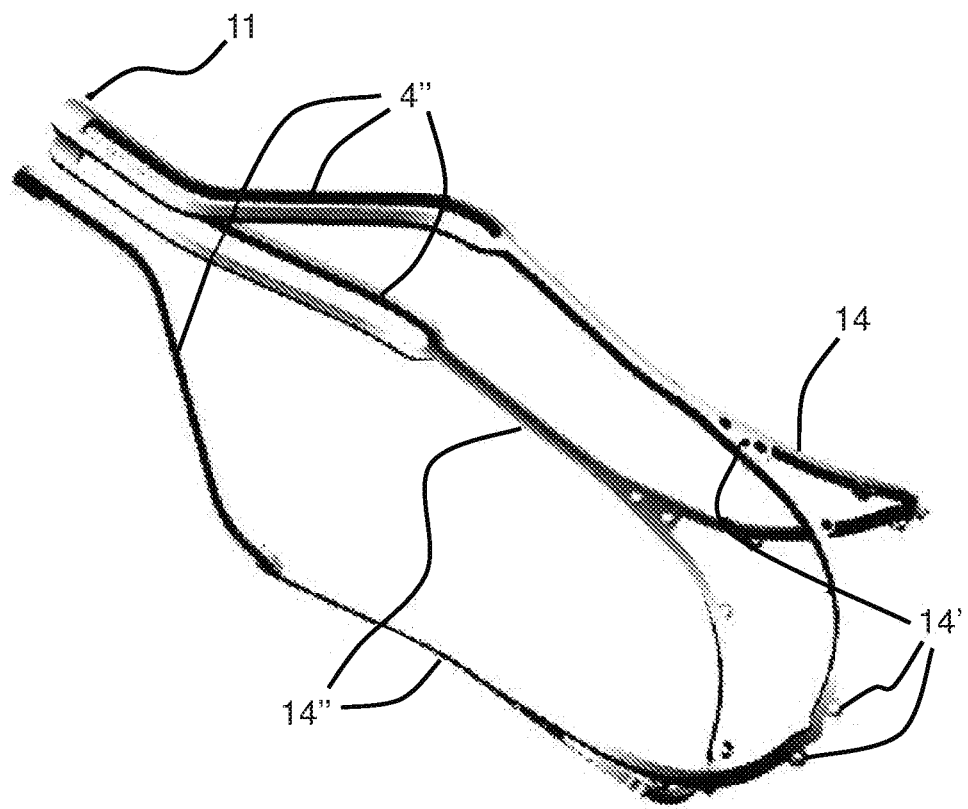
FIG. 7: Internal valve's support stent 14.
Figure 7A:
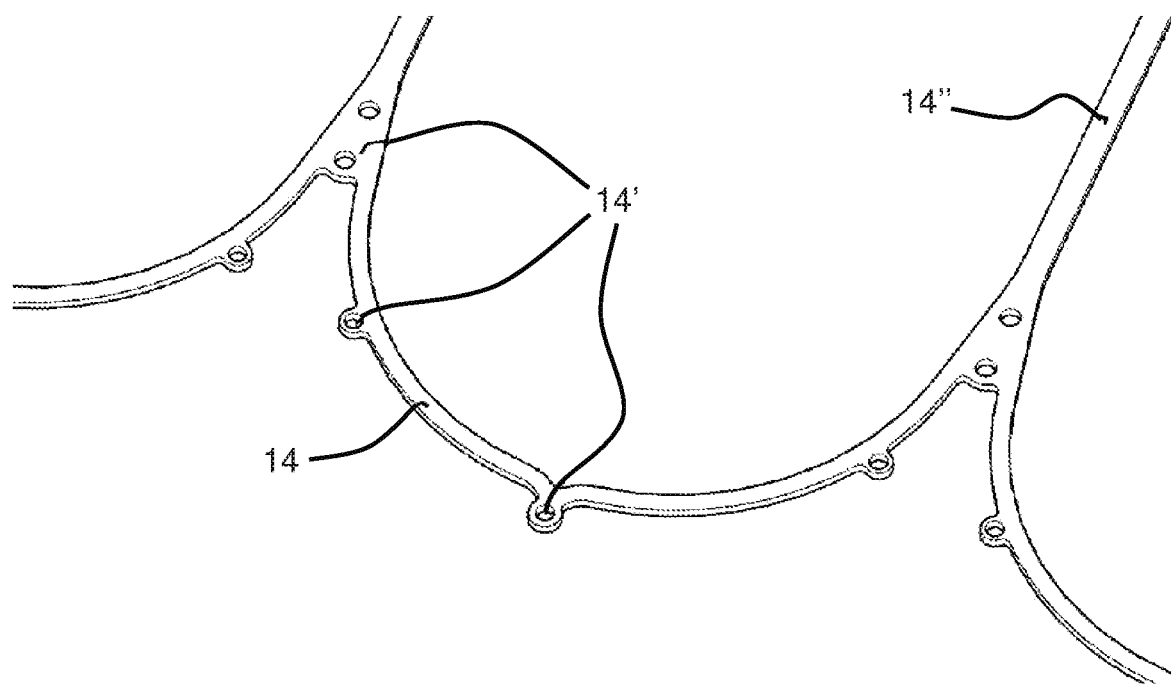
FIG. 7a: Internal valve's support stent 14: one configuration of inflow profile.
Figure 7B:
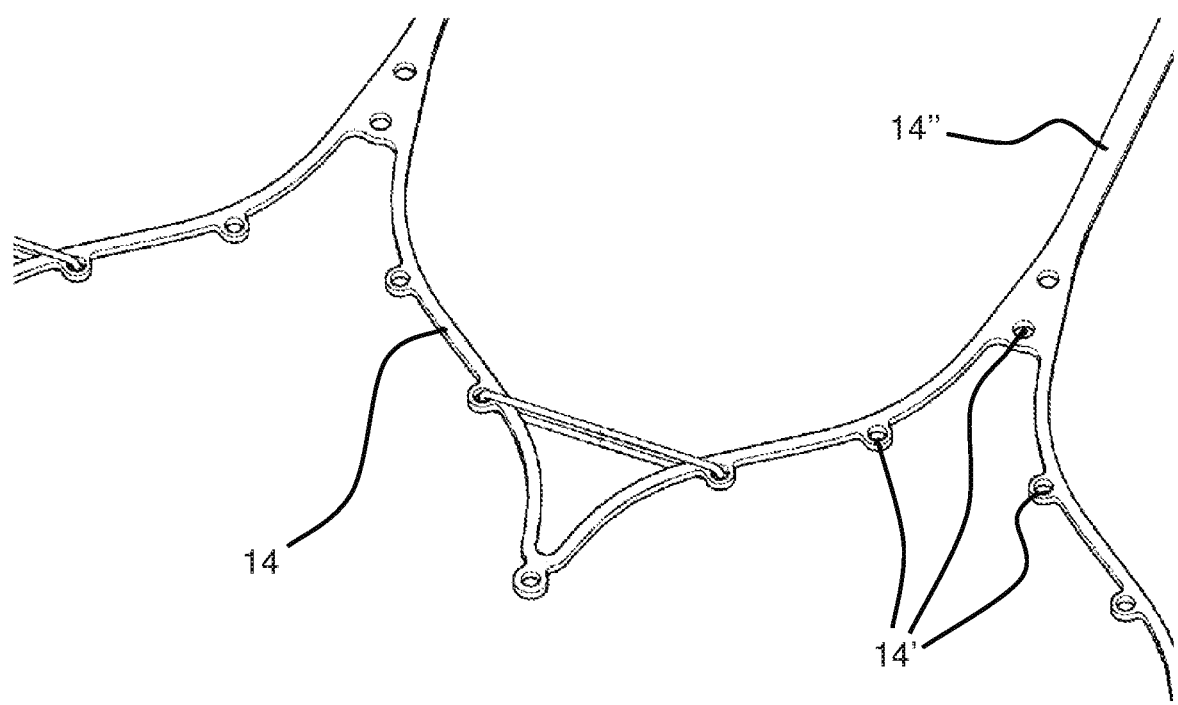
FIG. 7b: Internal valve's support stent 14: alternative configuration of inflow profile.
Figure 7C:
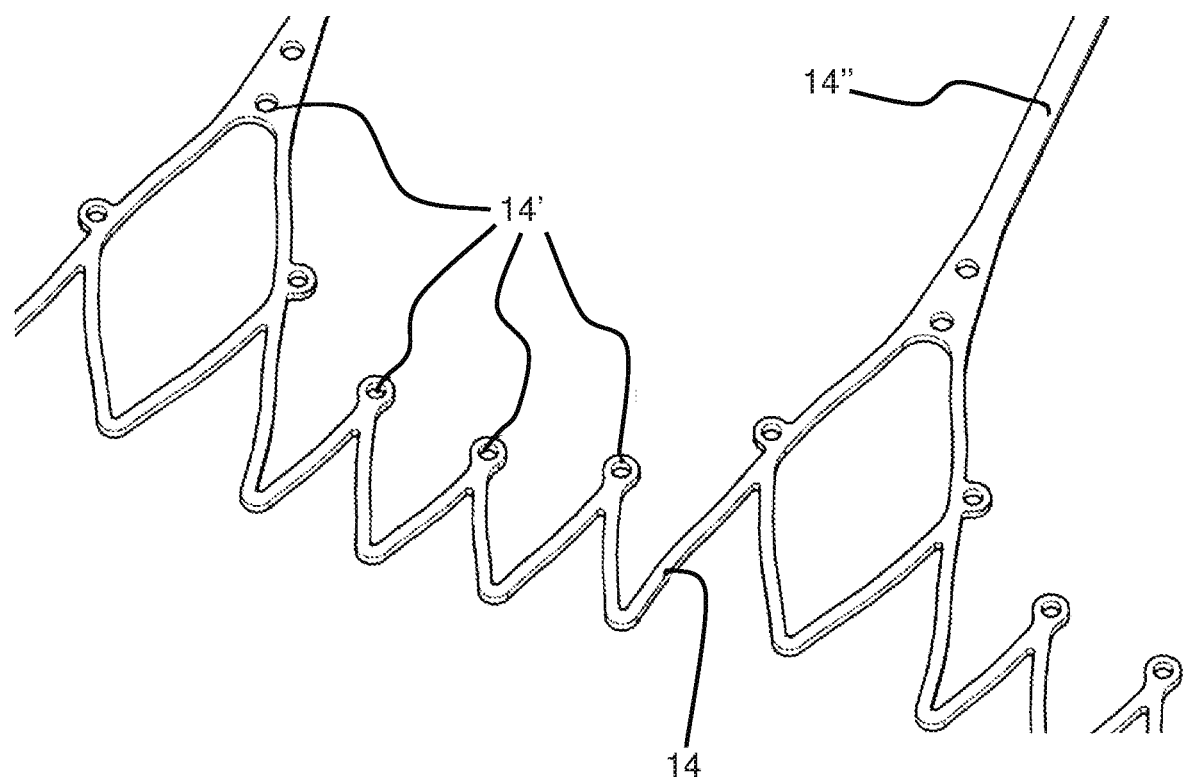
FIG. 7c: Internal valve's support stent 14: alternative configuration of inflow profile.
Figure 7D:
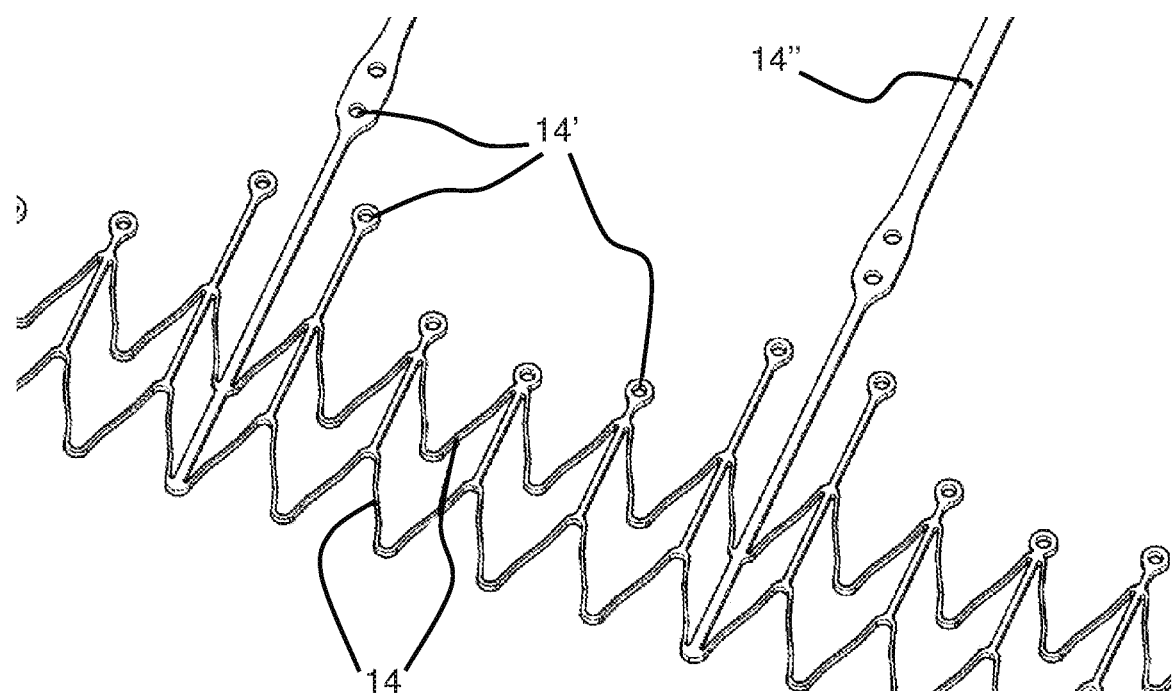
FIG. 7d: Internal valve's support stent 14: alternative configuration of inflow profile.
Figure 7E:
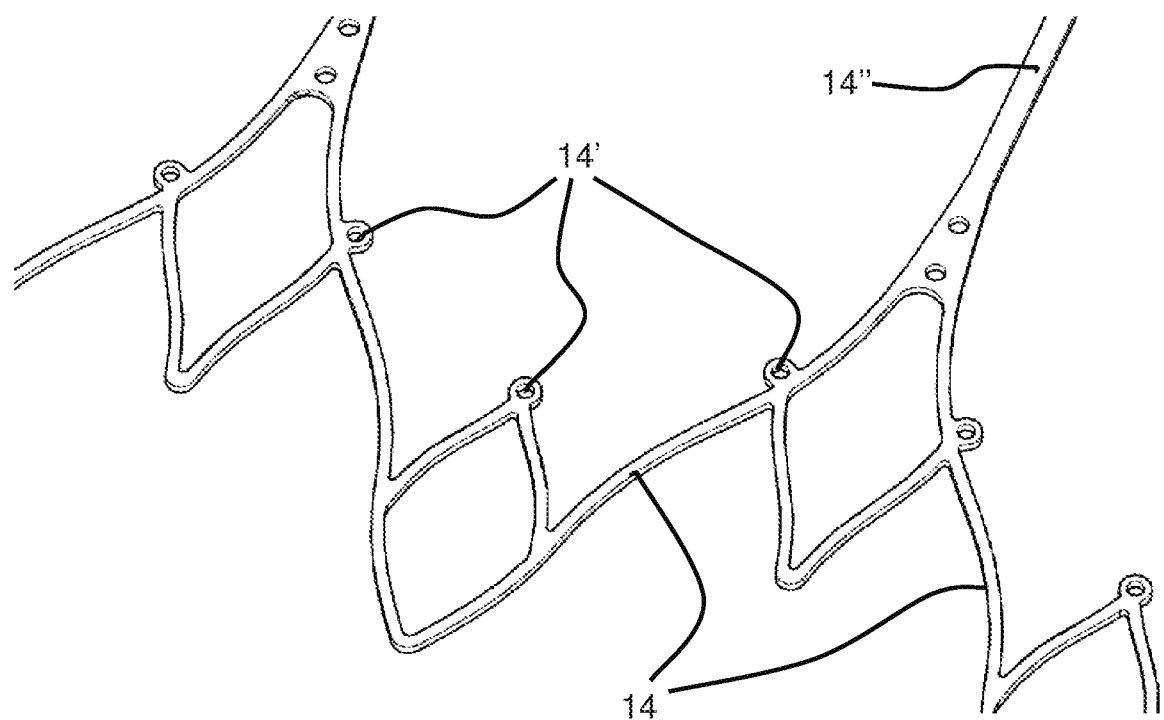
FIG. 7e: Internal valve's support stent 14: alternative configuration of inflow profile.

FIG. 7 shows the self-expandable internal valve's support stent 14, which supports both the commisures of the leaflet 7 and the overall inflow profile of the said leaflets 7 with specific joints 14', which contoures the structure from the external side. This configuration allows minimization of the pressure drop in the systolic phase thanks to a wide and cylindrical leaflet opening and minimization of the closure and leakage backflow regurgitation during the diastolic phase. The tethering struts 4" allow a direct joining with the internal shaft catheter 3' with adequate independence respect to the external support 5.

FIGS. 7a, 7b, 7c, 7d and 7e show alternative configurations of inflow profiles for ensuring at the same time adequate retrievability and radial stiffness.

Figure 8:
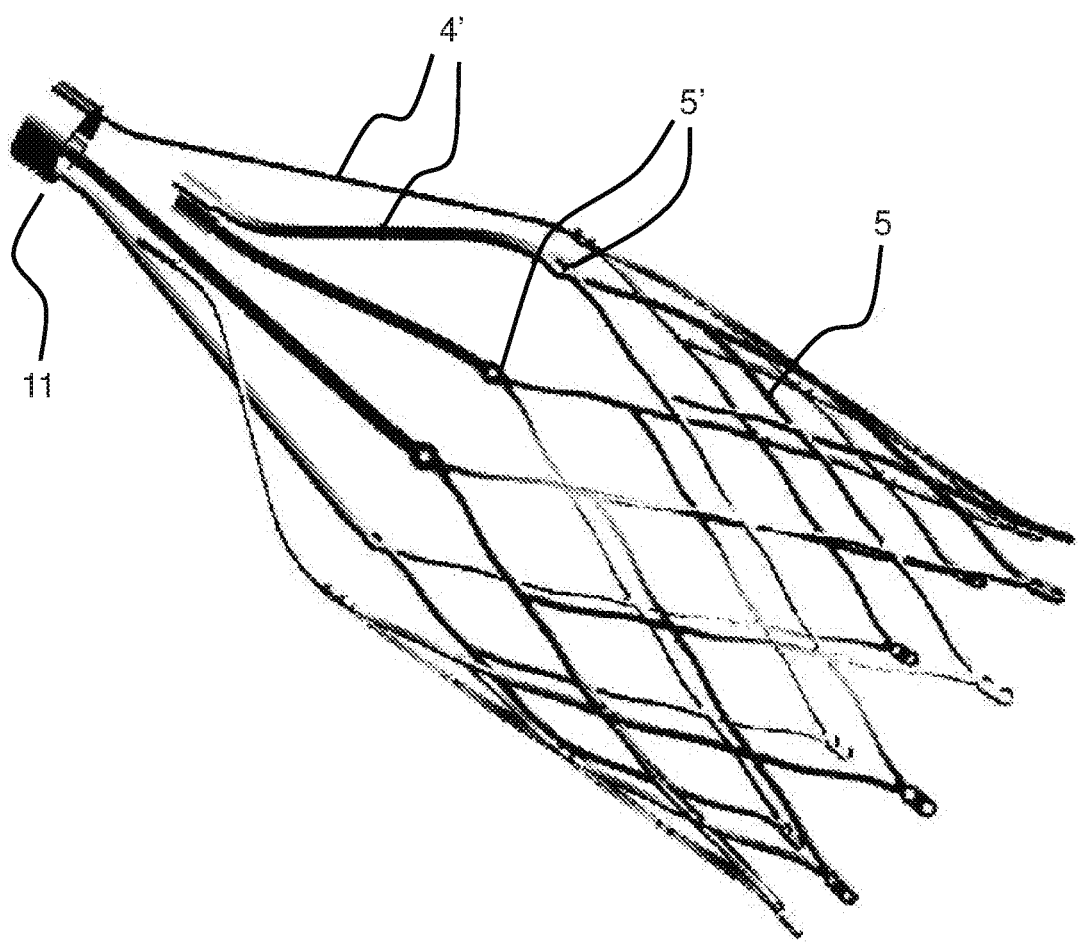
FIG. 8: External support structure 5.

FIG. 8 shows the self-expandable external support structure 5, which support the conveyor 6 and relevant filter mesh 12 at the anchoring holes 5' side and the coupling of the mesh 10 with the inflow side of the leaflets 7.

Figure 9:
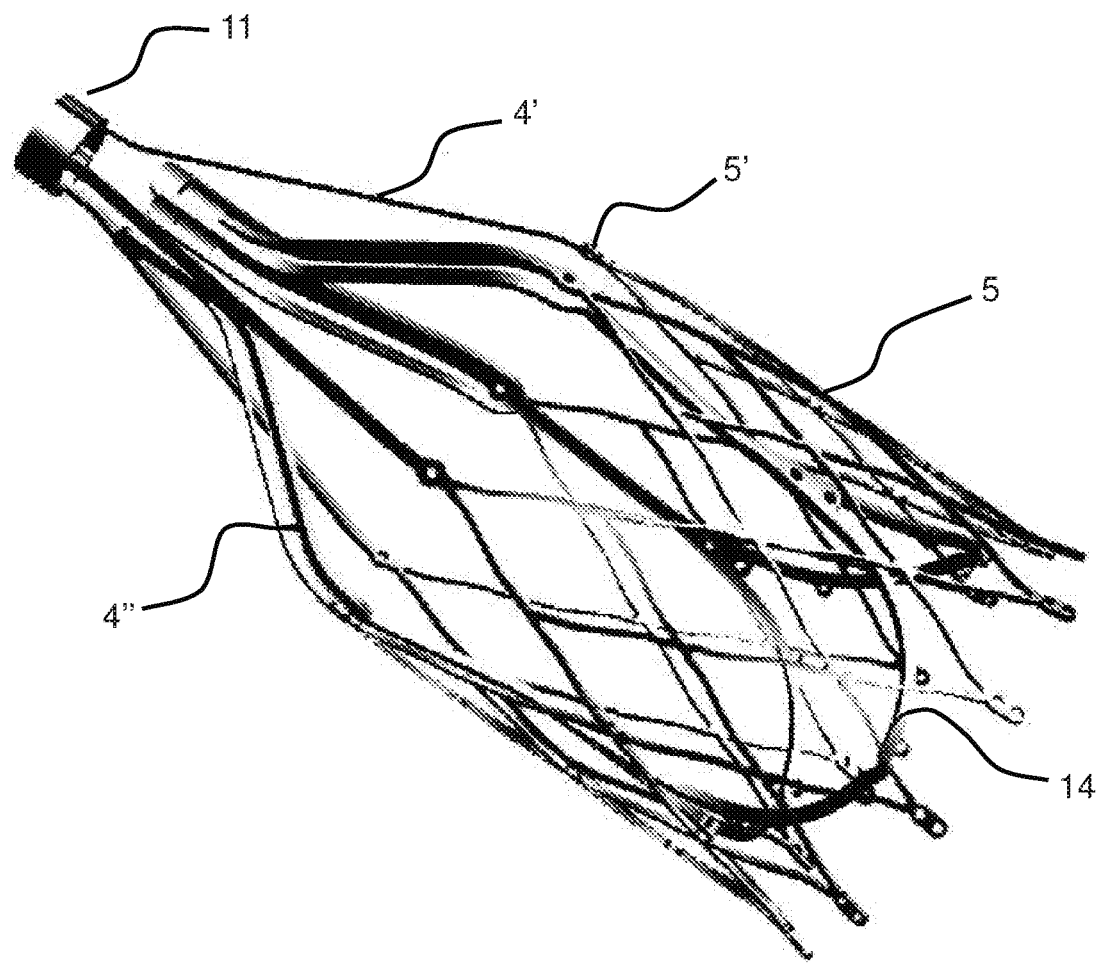
FIG. 9: External support structure 5 and valve's support stent 14.

In FIG. 9 both external 5 and internal 14 self-expandable structures are shown without the relevant mesh, in order to outline the mutual positioning of the tethering structures that joints them to the the internal catheter 3', together with the holes for connecting to the conveyor 6 and leaflets 7 elements.

Figure 9A:
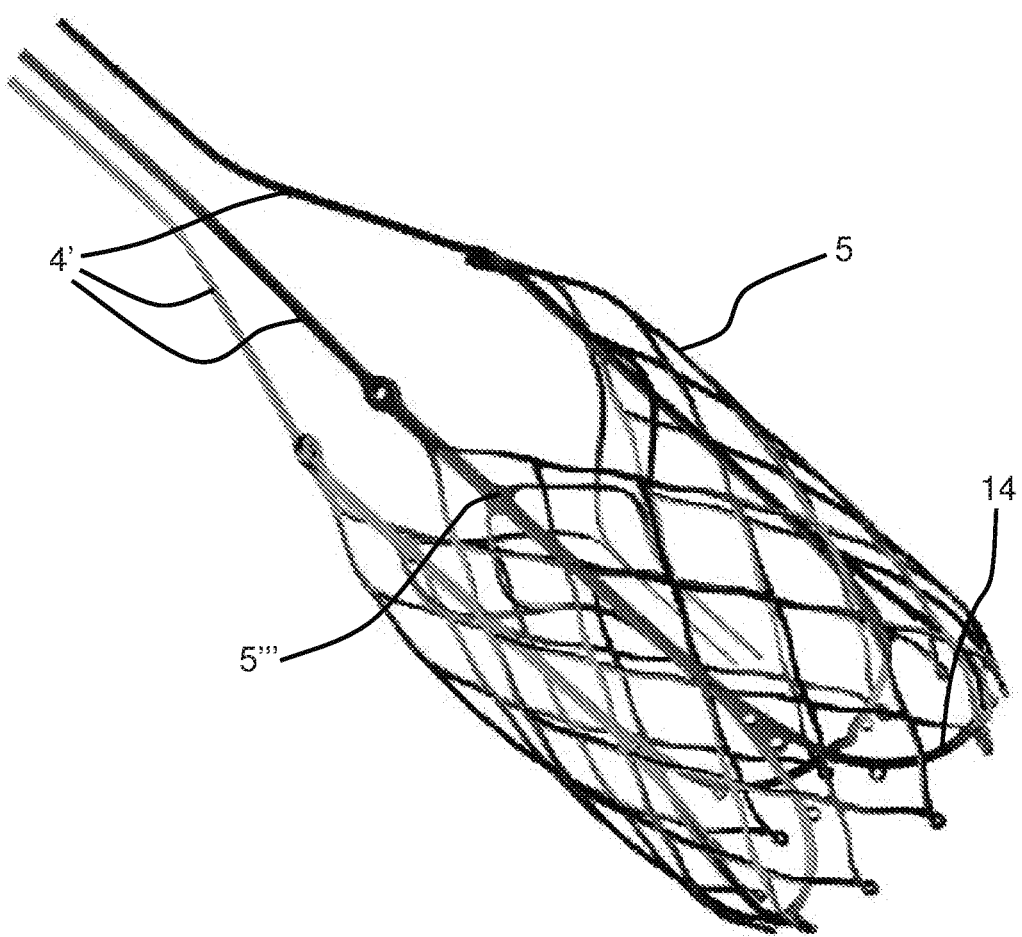
FIG. 9a: External support structure 5 and a combined internal structure 5".
Figure 9B:
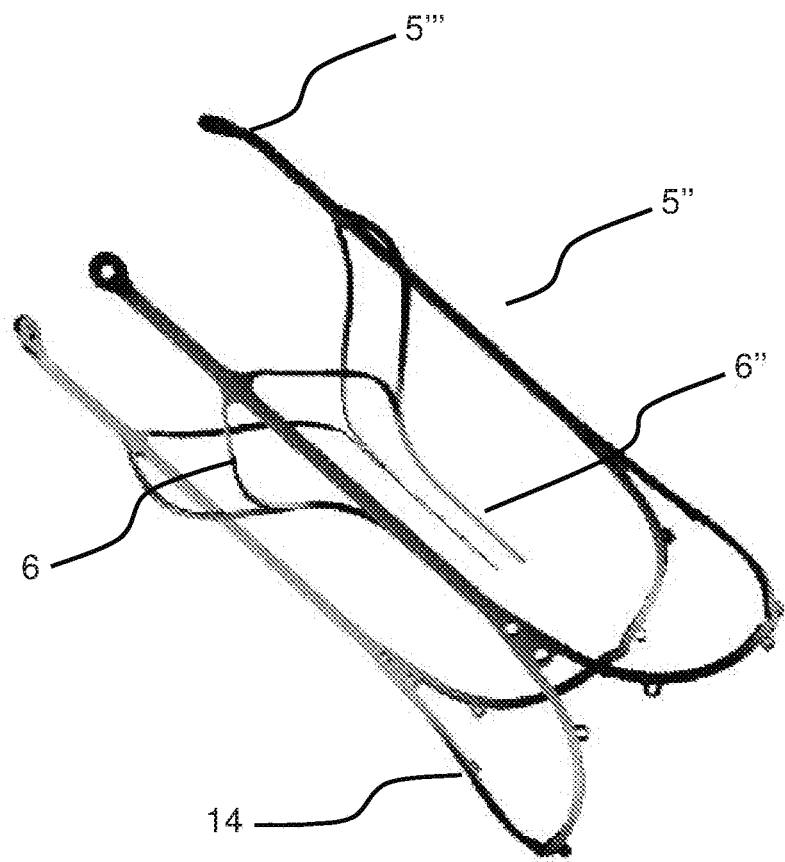
FIG. 9b: Combined internal structure 5" integrating the conveyor 6 and the valve's support stent 14. The structure 5" is anchored to the external support structure 5 by means of keyhole tethering struts 5'".

The internal elements, called conveyor 6 and valve's stent support 14, can be combined in a single element 5" to be joined to the external structure 5 by a tethered struts with keyholes 5'" as described in FIGS. 9a and 9b.

Figure 10A:
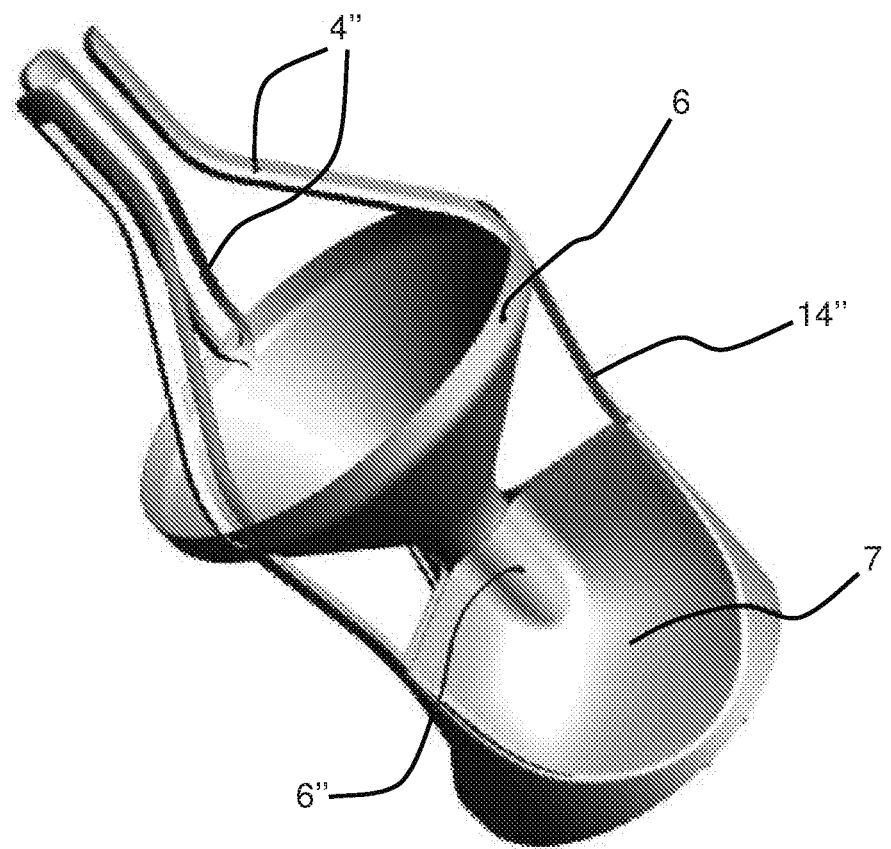
FIG. 10a: Internal structure of the device 4 showing the interaction of the conveyor with the prosthetic valve 15.
Figure 10B:
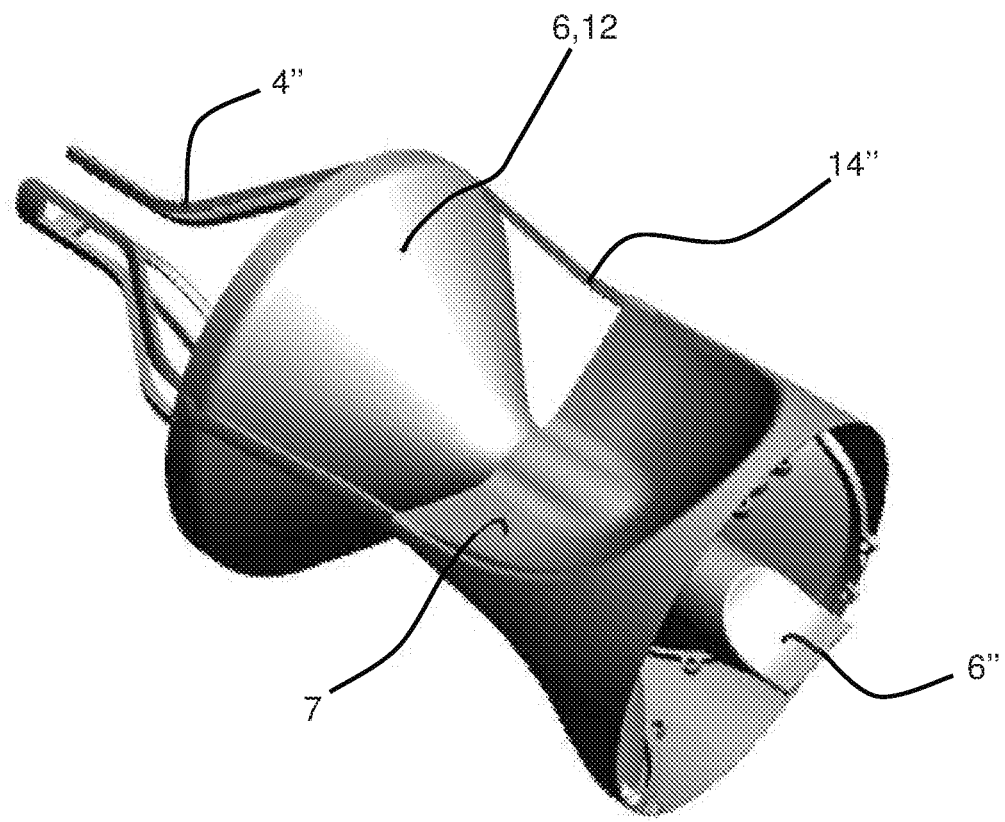
FIG. 10b: Different view of FIG. 10.

In FIG. 10, the outflow side of conveyor 6, supporting the filter 12, and the prosthetic valve 15 elements are shown, together with the self-expandable internal valve's support stent 14 and the tethering struts connecting said structure to the internal shaft catheter 3'.

As far as concerns the conveyor and filter elements, the conical shape of the conveyor guarantees first a smooth and easy crossing by the devices loaded with external catheter different than the external 3; second, it is covered with a filter 12 of adequate mesh and surface, in order to minimize relevant pressure drop in the systolic phase and filter any possible embolization debris deriving from the procedure and maintain it in the collection chamber obtained between the mesh 12 and 10; third, it guarantees a smooth retrieve. The distal end of the conveyor is cilindrical with axis aligned with the diseased valve to be treated, to guarantee a proper alignment of the loaded device. Furthermore, this cilindrical part has radial compliance adequate to minimize the force to be applied for loading and retrieving the device through the delivery system.

In FIG. 10a the same elements are viewn from the inflow side (ventricle view), with the bi-directional normally closed valve at the distal part of the conveyor shown, that guarantees no flow both in systole, to impede any embolization to cross the device 4, nor in diastole, to minimize overall leakage, whilst allowing the loaded device crossing through the device 4.

As far as it concerns the valve, FIGS. 10 and 10a show the prosthetic valve body 15 from the outflow and inflow side. The trileaflet configuration was selected, with leaflets made of a low thickness polymeric fabric elastomerically coated and installed outside the supporting structure 14 in order to guarantee a wide leaflet cylindrical open configuration. This design configuration guarantees optimal pliability/foldability and at the same type relatively low extensibility, thus optimal hemodynamics and mechanical characteristics.

Design and materials allow adequate hemodynamic performance in terms of low pressure drop in systole, thanks to the large orifice area and leaflets foldability, and low regurgitation in diastole, thanks to the leak free characteristic of the leaflets and relevant foldability that allows a proper coupling at closure of the said leaflets respect to the distal conveyor leak free tube body 6".

Figure 11:
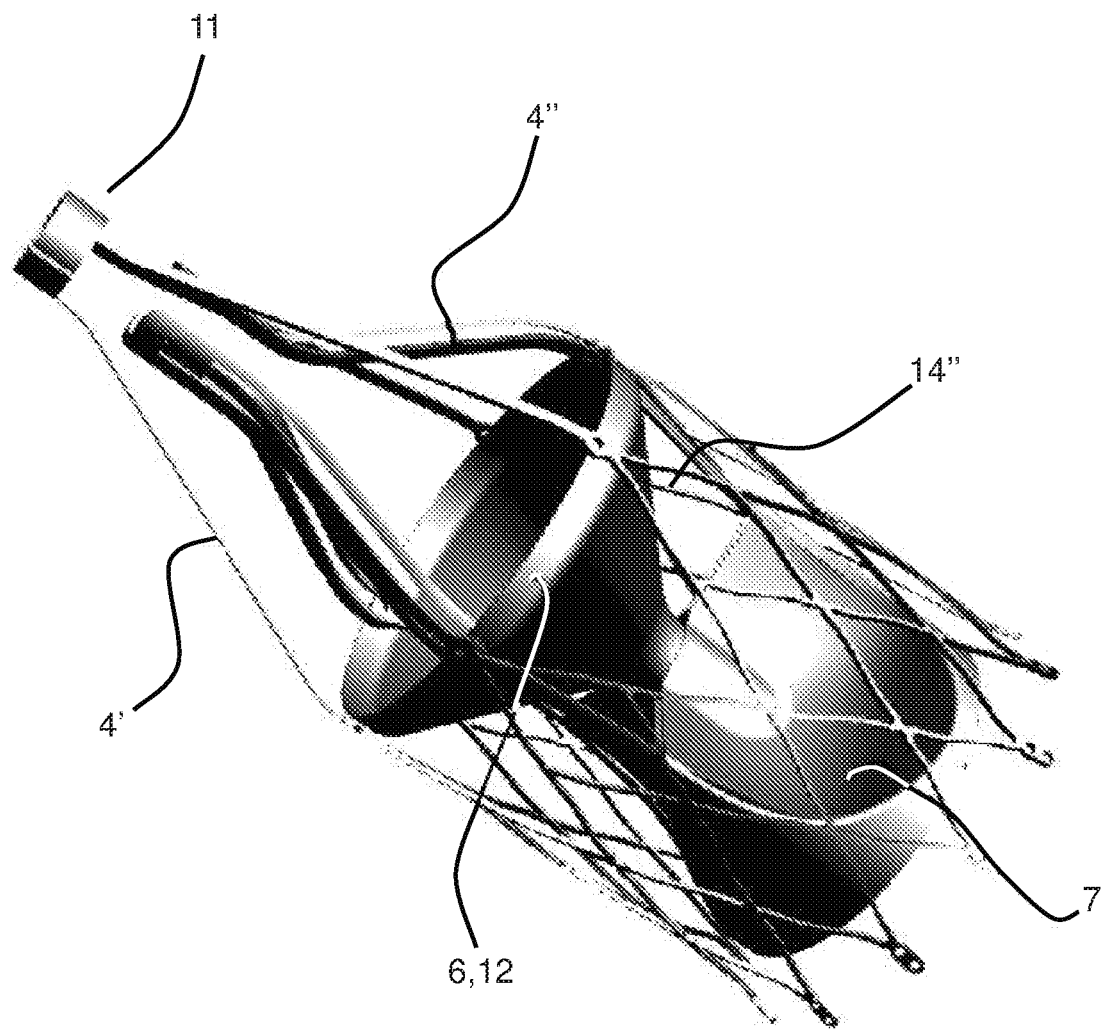
FIG. 11: Device 4 assembled without the antiembolic filter mesh 10.

FIG. 11 shows the configuration of the device 4 assembled without the mesh 10, in order to visualize the mutual positioning of the conveyor/filter and of the valve respect to the relevant external 5 and valve's support stent 14 support structures.

Radiopaque markers are placed in order to better detect specific locations, such as the posts and side access, and internal catheter locations, such as the aortic arch level. Materials, joining mechanism and number of elements are selected based at the state of the art and based on the current procedures.

FIGS. 12 to 15 show an alternative embodiment, configured as well as the hybrid one with a conveyor internal to the body, in order to minimize overall length, but with both the external support structure 5 and the conveyor 6 made of a superelastic metallic mesh, therefore referred as mesh embodiment. Another difference respect to the hybrid embodiment is that in the mesh embodiment the external support structure 5 directly provides an anchoring surface for the leaflet of prosthetic valve 15.

Figure 12:
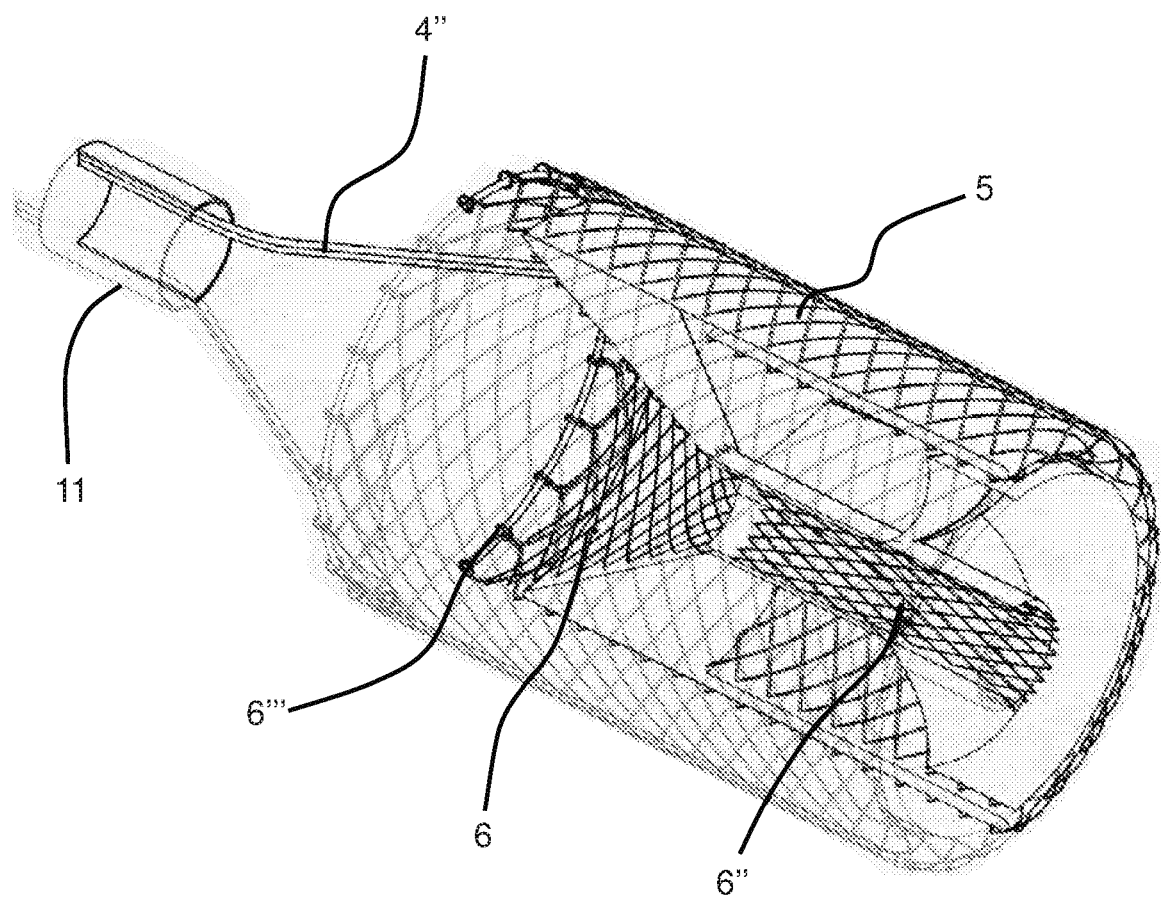
FIG. 12: Device 4 assembled with a self-expandable mesh

FIG. 12 shows a lateral view of the mesh assembly, with the external cylindrical structure 5 and the mesh 10, the conveyor 6 and relevant mesh 12, the prosthetic valve 15, together with the relevant coupling between the elements.

The coupling elements of the superelastic metallic external structure 5 are as follows: a tethering structure 4', which is permanently joined to the internal catheter 3' by means of a ring 11, sustains the external structure 5 and the inflow side of the conveyor 6, whilst allowing the mutual sliding of the elements to allow proper self expanding and retrieval; a cylindrical tube mesh 10, acts as a mutual joint elements between the external structure 5 and the prosthetic valve 15, namely with sewing/ultrasound welding them at the inflow and outflow sides to the tube 10 and to the valve along its inflow side profile.

Figure 13:
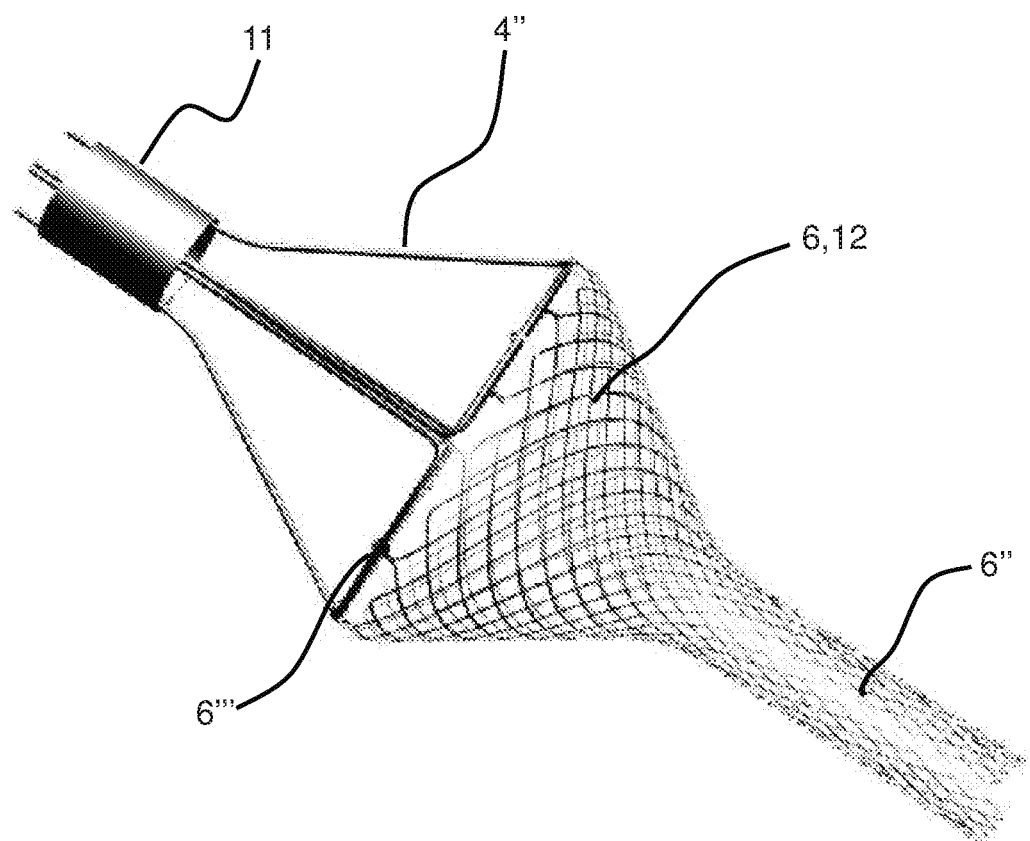
FIG. 13: Device as in FIG. 12 only with conveyor.

In FIG. 13 the conveyor 6 is shown in its coupling to the internal catheter 3' by means of the tethering structure 4", in its conical part and in relevant conveyor distal tube 6" equipped with the bi-directional normally closed valve. The same features already depicted for the preferred assembly here apply.

Figure 14:
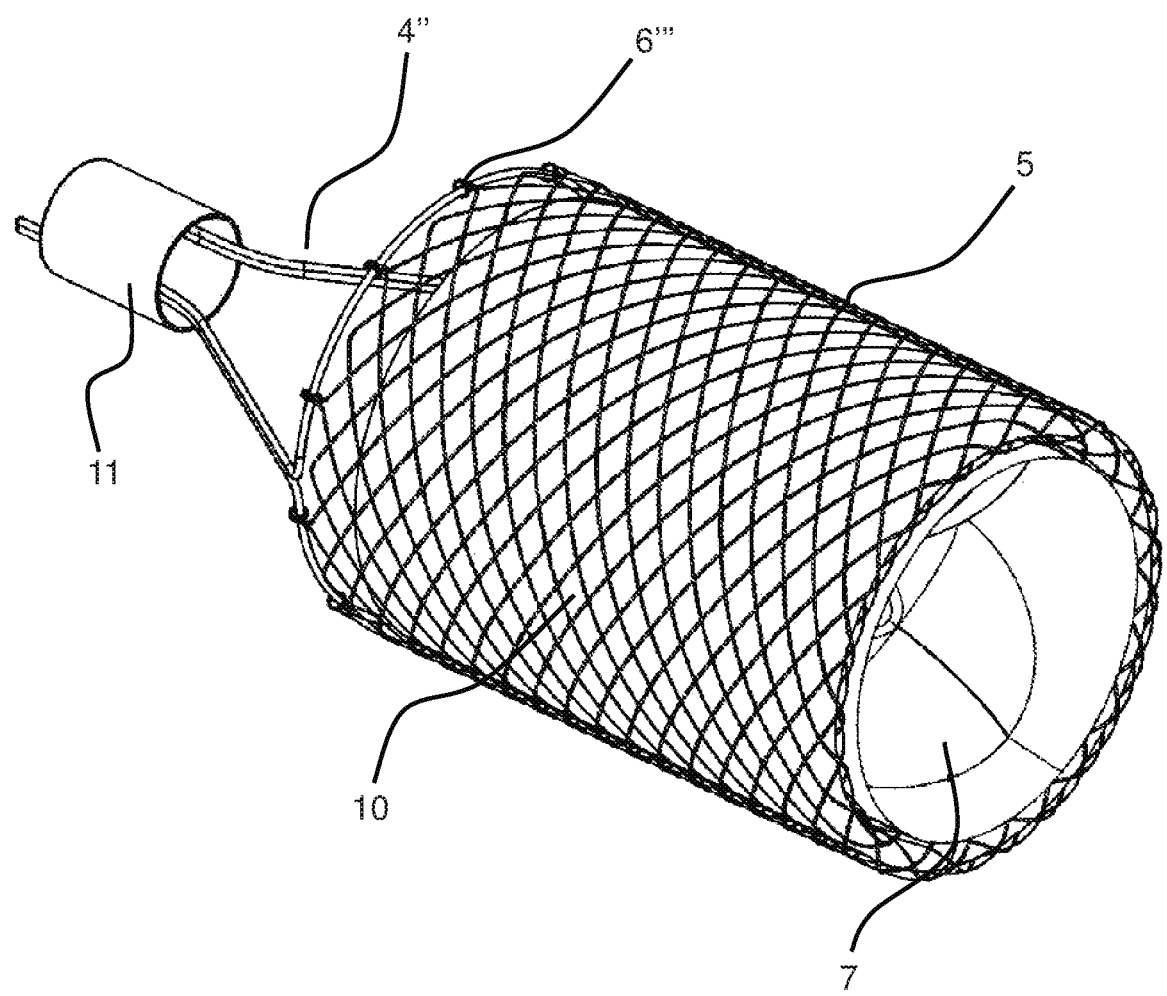
FIG. 14: Device as in FIG. 12 with external support structure and internal valve anchored to its internal wall.

In FIG. 14 the external support structure 5 and internal valve's support stent 14 anchored to its internal wall are shown. This embodiment is different respect to the hybrid one because it misses an internal metallic support structure in order to optimize the low profile characteristics of the device rather than having an independent valve anchoring.

Figure 15:
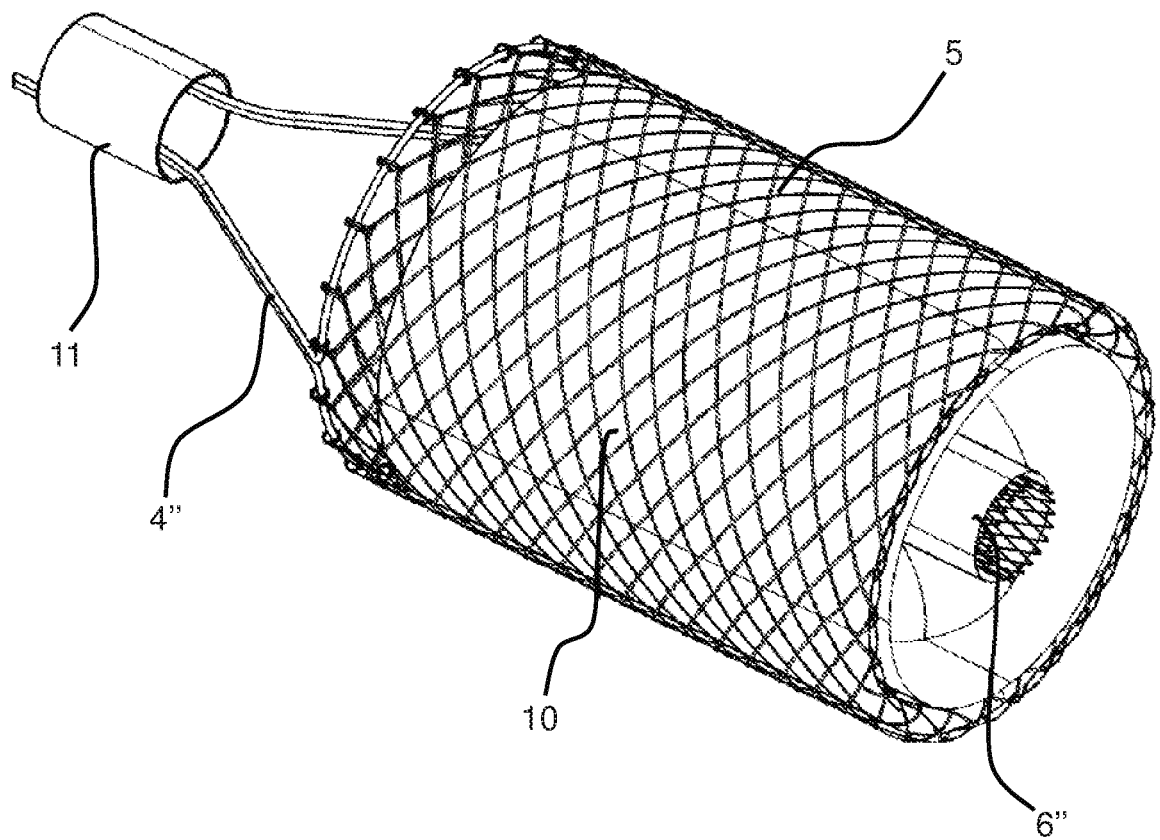
FIG. 15: Device as in FIG. 12 only represented with external support structure.

In FIG. 15 the sliding coupling amongst the external support structure 5 and the tethering struts 4" is shown from the outflow side.

Figure 16:
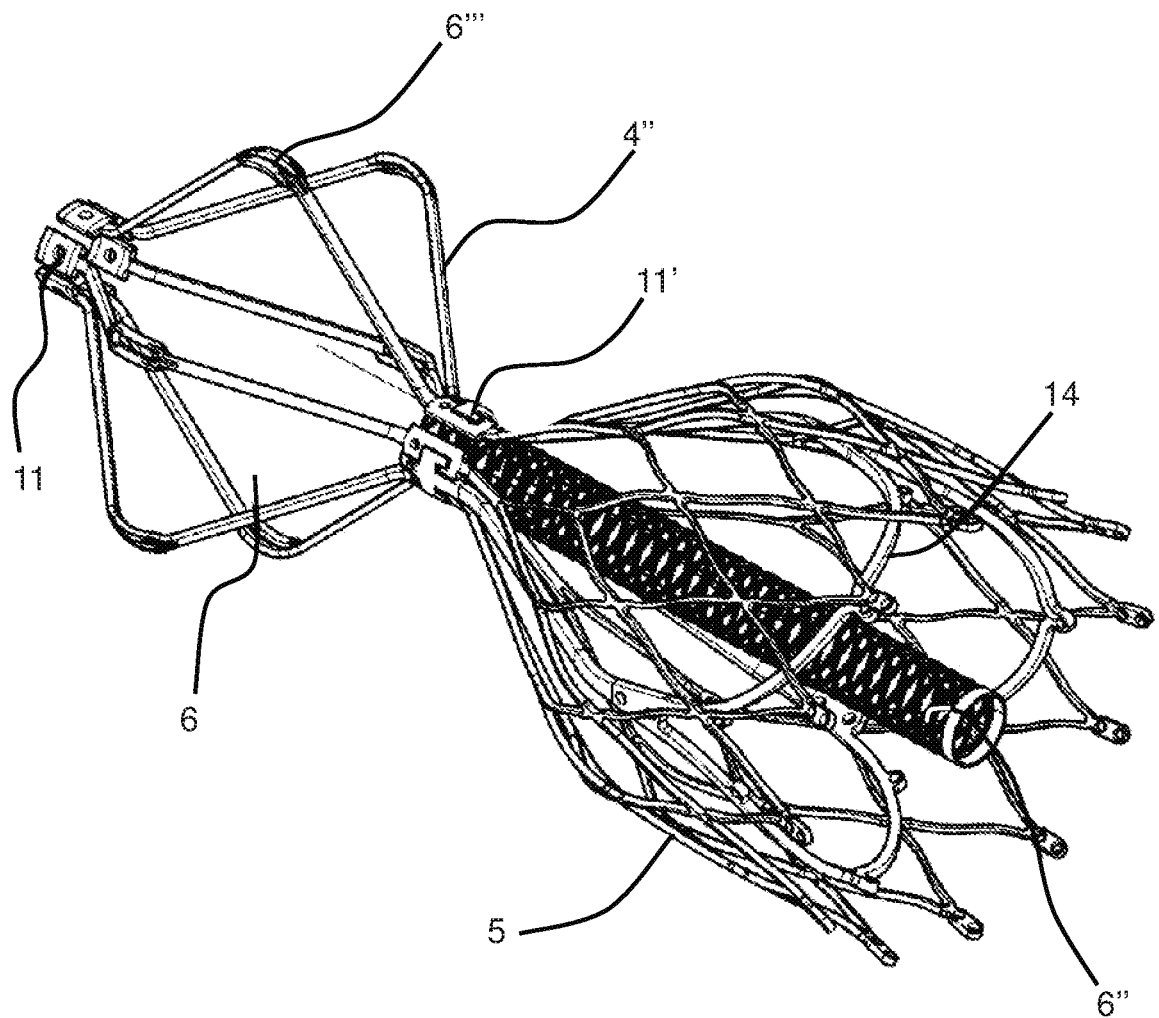
FIG. 16: Device 4 with the convejor system placed outside the device. In this embodiment it has been placed in series sequentially and proximally to the device.
Figure 16A:
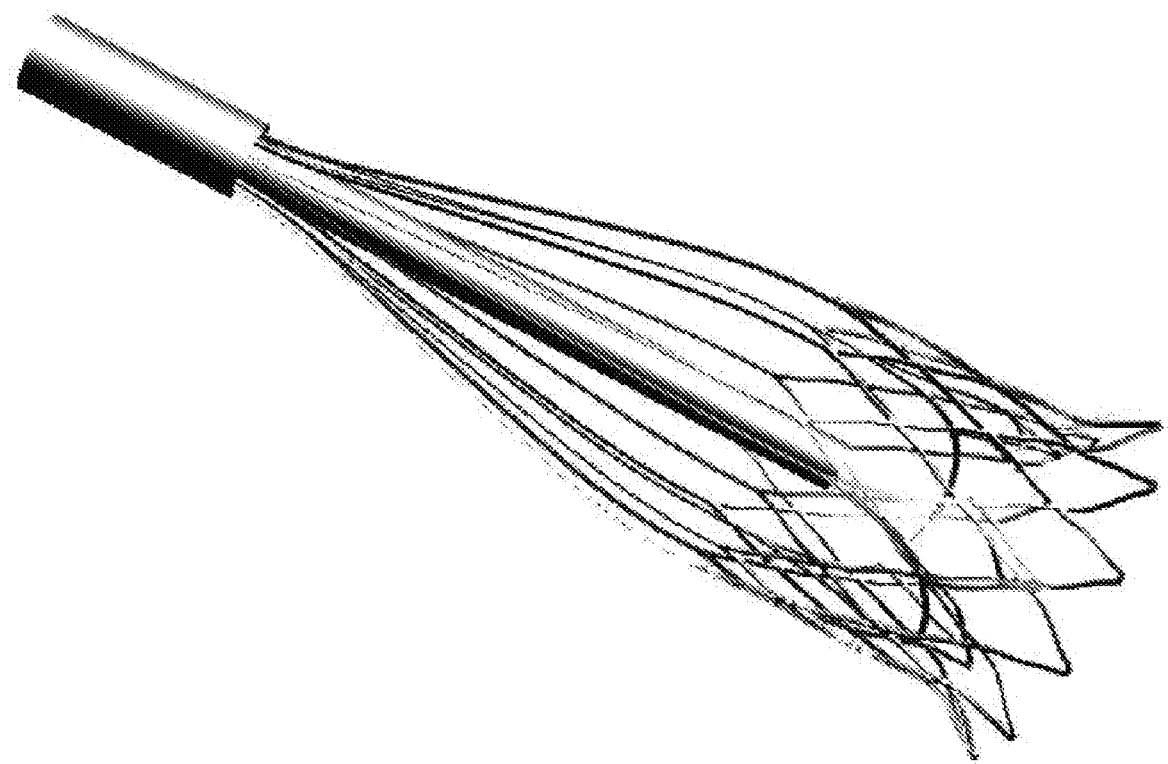
FIG. 16a: Another embodiment of the device 4 with the convejor system placed outside the device.
Figure 16B:
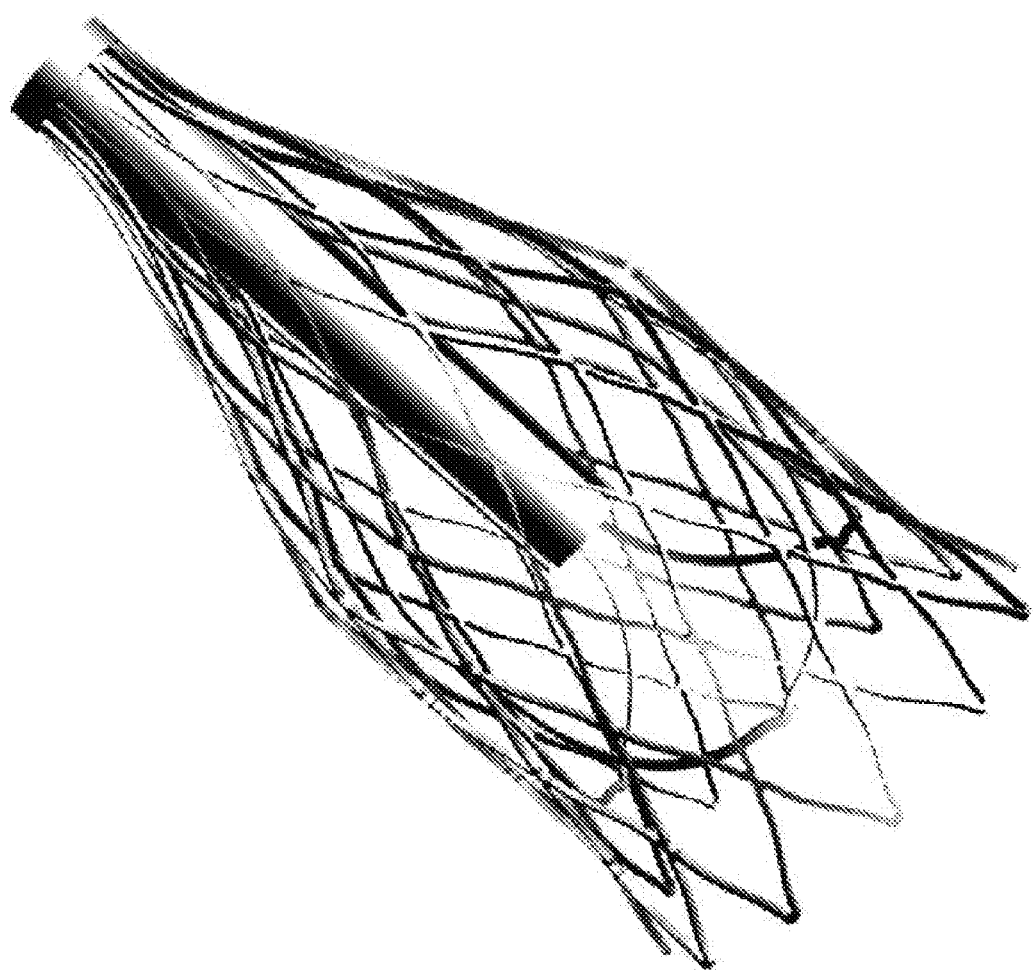
FIG. 16b: Another embodiment of the device 4 with the convejor system placed outside the device.
Figure 16C:
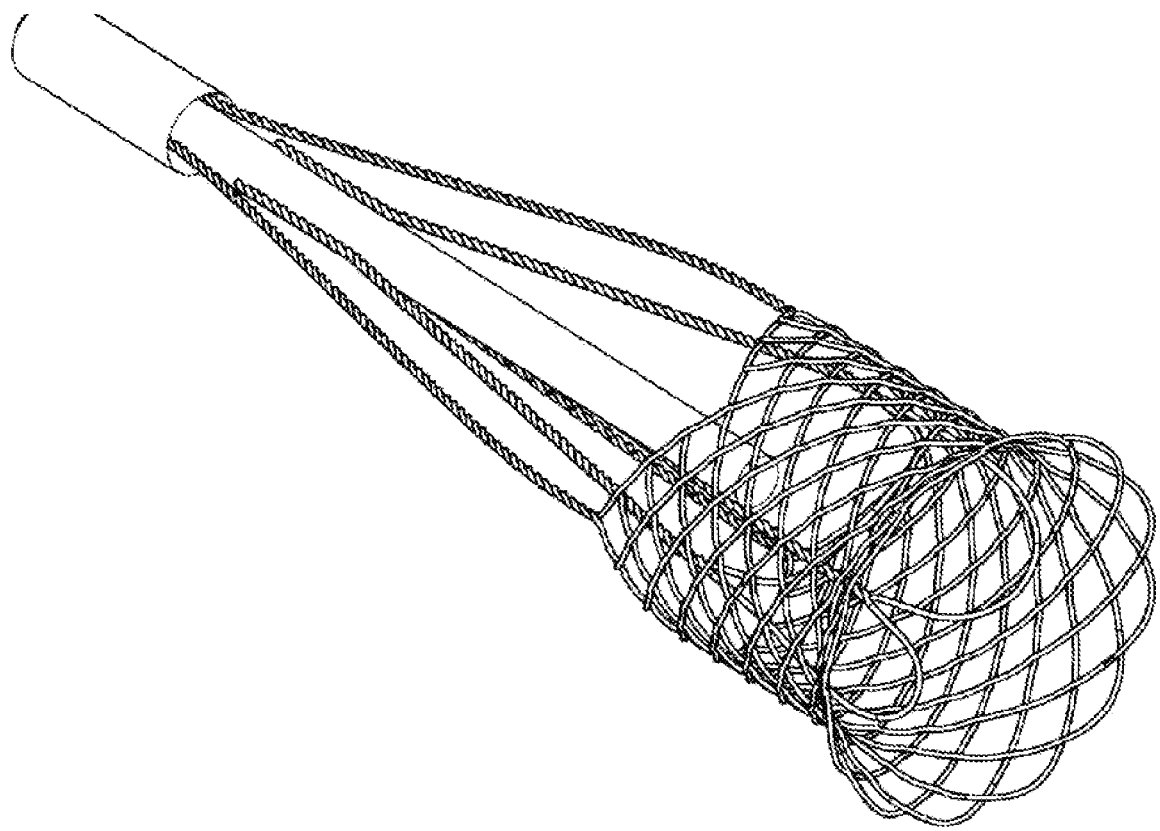
FIG. 16c: Another embodiment of the device 4 with the convejor system placed outside the device.
Figure 16D:
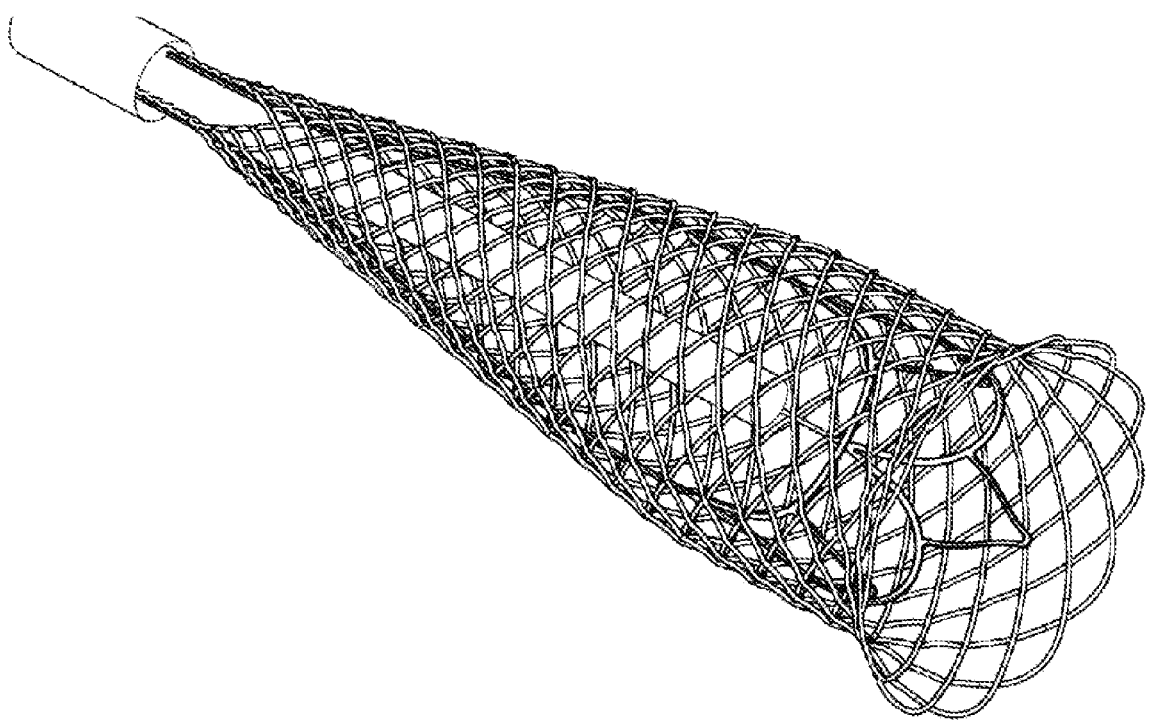
FIG. 16d: Another embodiment of the device 4 with the convejor system placed outside the device.
Figure 16E:
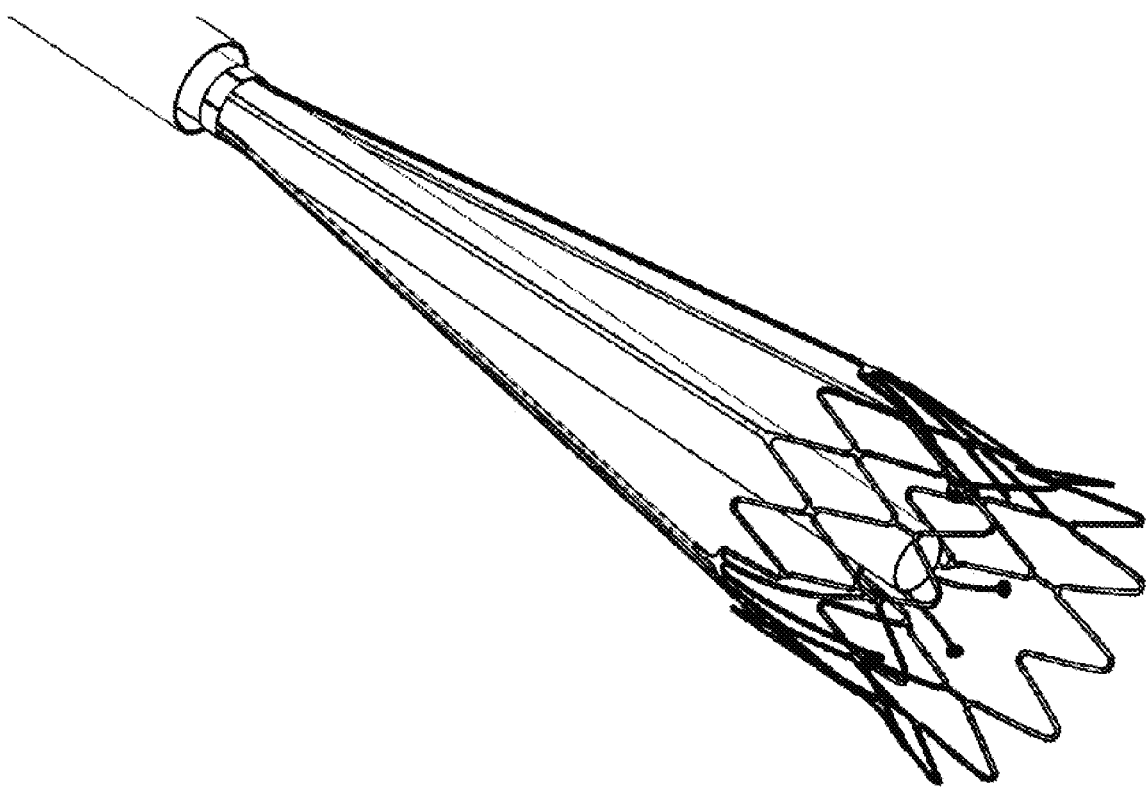
FIG. 16e: Another embodiment of the device 4 with the convejor system placed outside the device.
Figure 17:
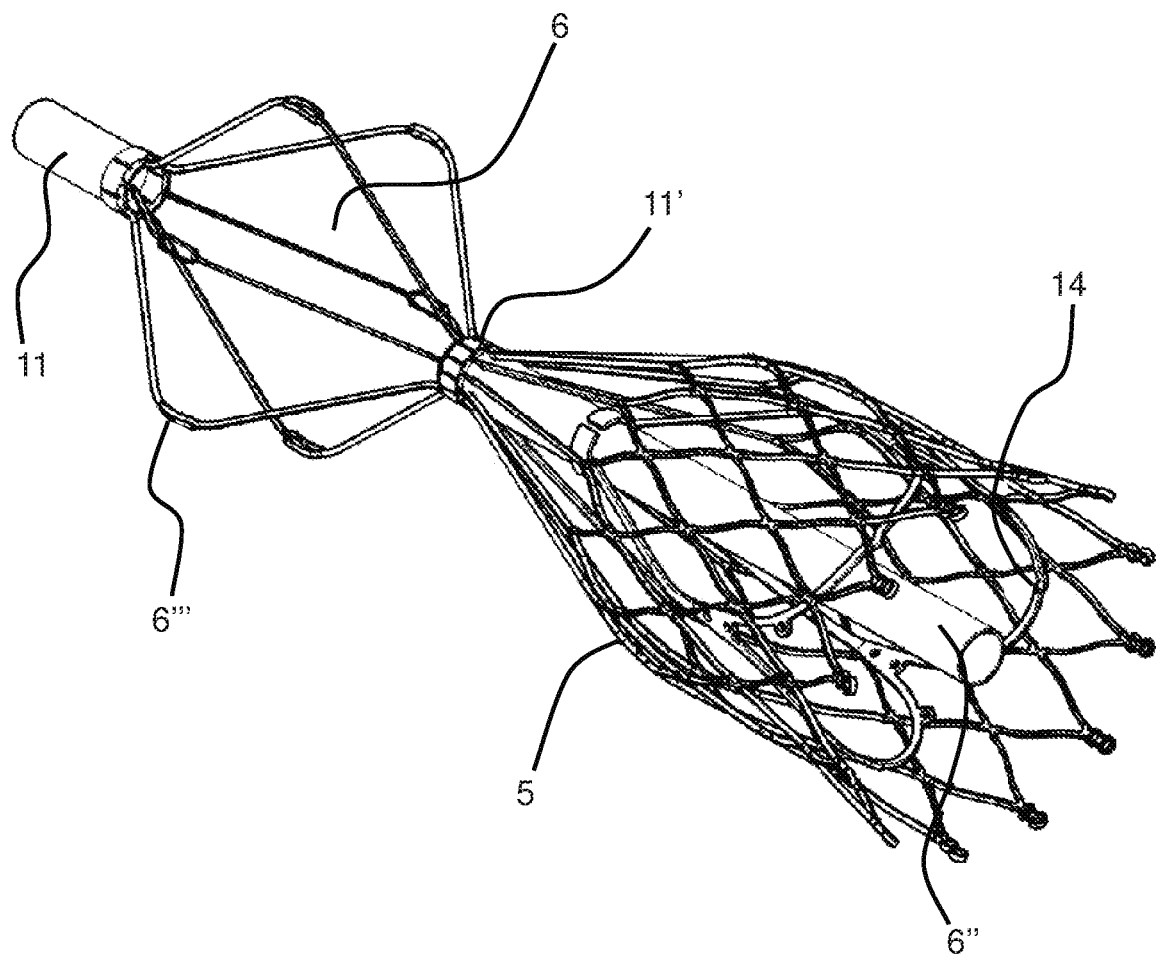
FIG. 17: Device 4 as in FIG. 16 but without the distal conveyor's tube with bi-directional normally closed valve 6" and the valve's support stent 14.
Figure 18:
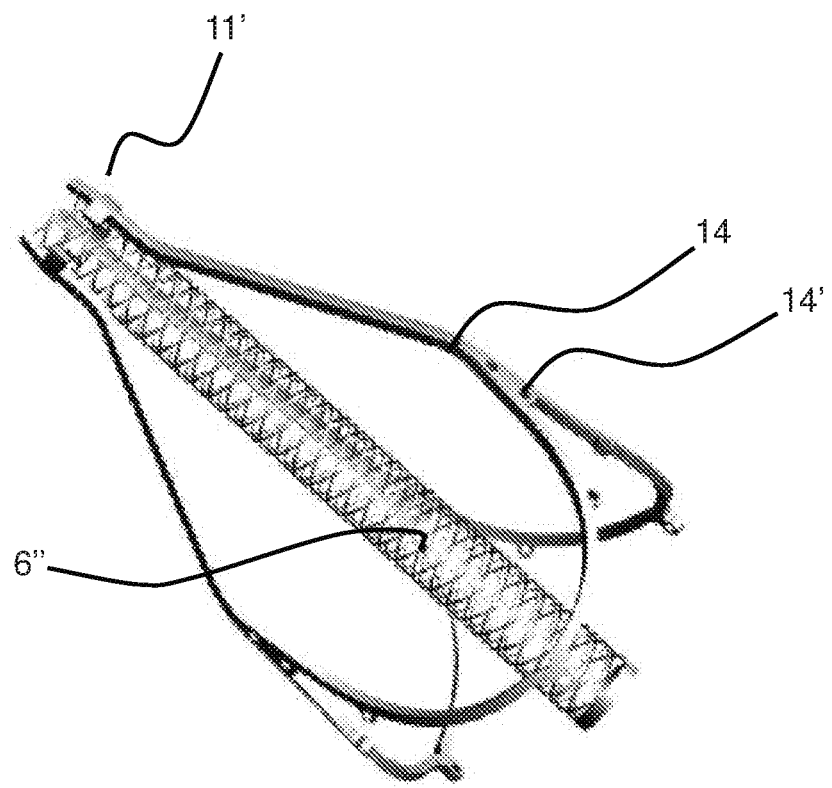
FIG. 18: Internal valve's support stent 14 and distal conveyor's tube with bi-directional normally closed valve 6".

FIGS. 16 to 18 show a device 4 derived from the hybrid, but with the conveyor 6 system placed proximally outside the device.

As one can see in FIG. 16, this embodiment can guarantee, in principle, an alignment of the loaded device better than the previous ones due to a longer distal conveyor tube and an easier retrieval inside small caliper external catheter 3 thanks to the reduced number of elements put one inside the other. At the same time, due to the higher length respect to the embodiments with internal conveyor, the coupling at 11' must be flexible in order to follow the aortic arch pattern at the proximal conveyor side, whilst guaranteeing a stable anchoring to the aorta at the distal side.

FIGS. 16, 16*a*, 17, 18 show the elements similar to the hybrid ones (namely the coupling amongst the prosthetic valve 15 and its valve's support stent 14, the coupling amongst the mesh 10 and the external structure 5) and the main differences: the conveyor cone 6 is proximal, it is placed outside of the external structure 5, and it is half distally covered with a filtering mesh that can have only the mechanical function of driving the movement of the loaded devices towards the internal lumen of the conveyor; the antembolic filter mesh 12, viceversa, is in the conical part of the external structure, distal respect to the ring 11'.

In the following figures, some alternative embodiments of the external support 5 and valve's support stent 14 are shown, without the conveyor system.

FIGS. 16*b*, 16*c*, 16*d* and 16*e* show, respectively, two laser cut and two braided alternative embodiments of the external structure 5 of the hybrid device 4, with different ratio between diamonds and straight elements in order to be more oriented to radial stiffness or retrievability characteristics.

Figure 16F:
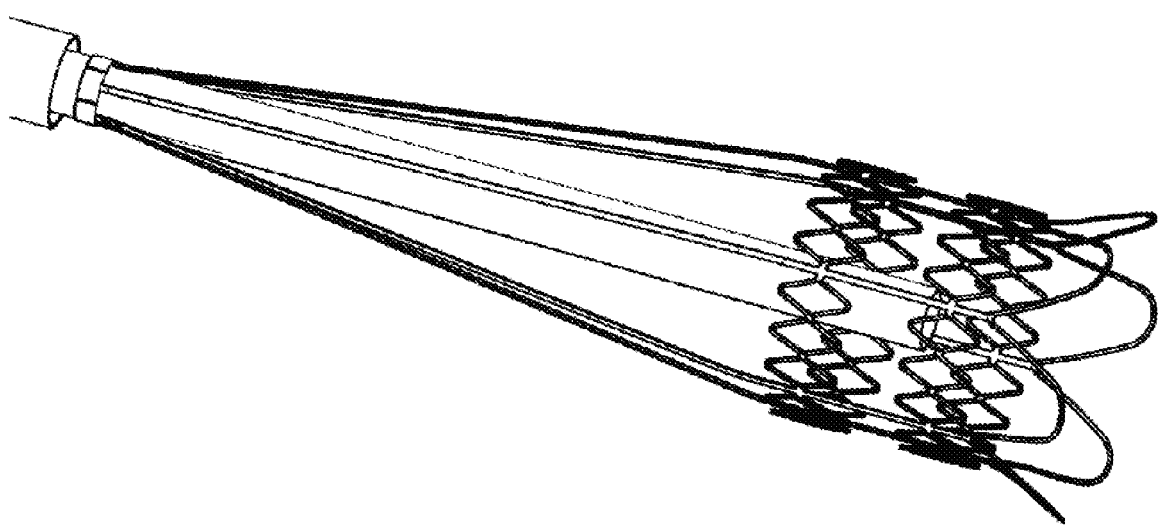
FIG. 16f: Another embodiment of the device 4 with the convejor system placed outside the device.

FIG. 16*f* shows a self expanding structure that combines the characteristics of the external 5 and valve's stent 14 support structures in one, devoting the last one on holding only the leaflets posts. This embodiment is intended to minimize the radial thickness of the supporting structure in order to maximize the retrievability. FIG. 16*g* shows a self expanding structure similar to the hybrid mesh, in which two diamond structures at the inflow and outflow sides of the valve are joined by linear elements in order to avoid overall length variation of this region at retrieval and a skirt element.

Figure 19:
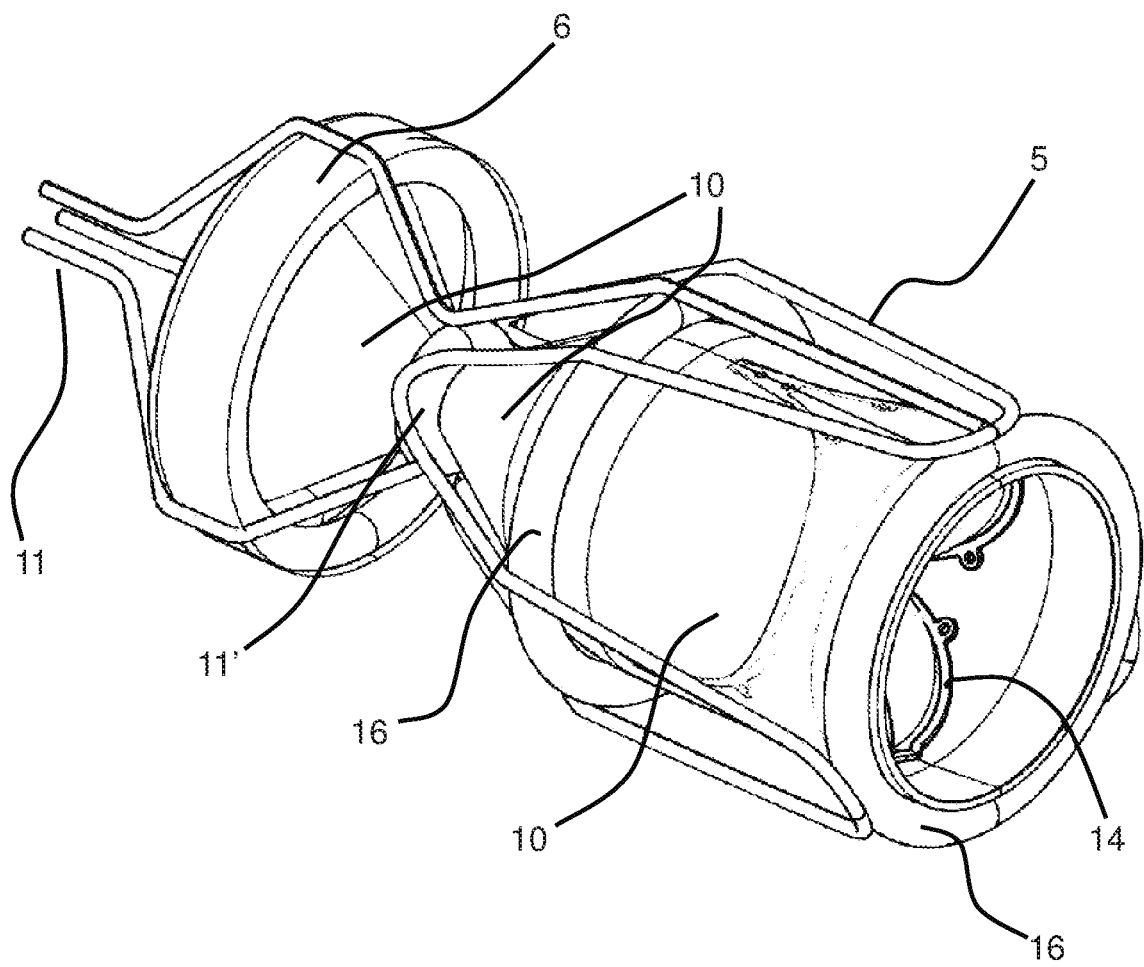
FIG. 19: Device 4 with inflatable structures supporting the device. The conveyor is placed proximally to the device 4 as described in FIG. 16.
Figure 20:
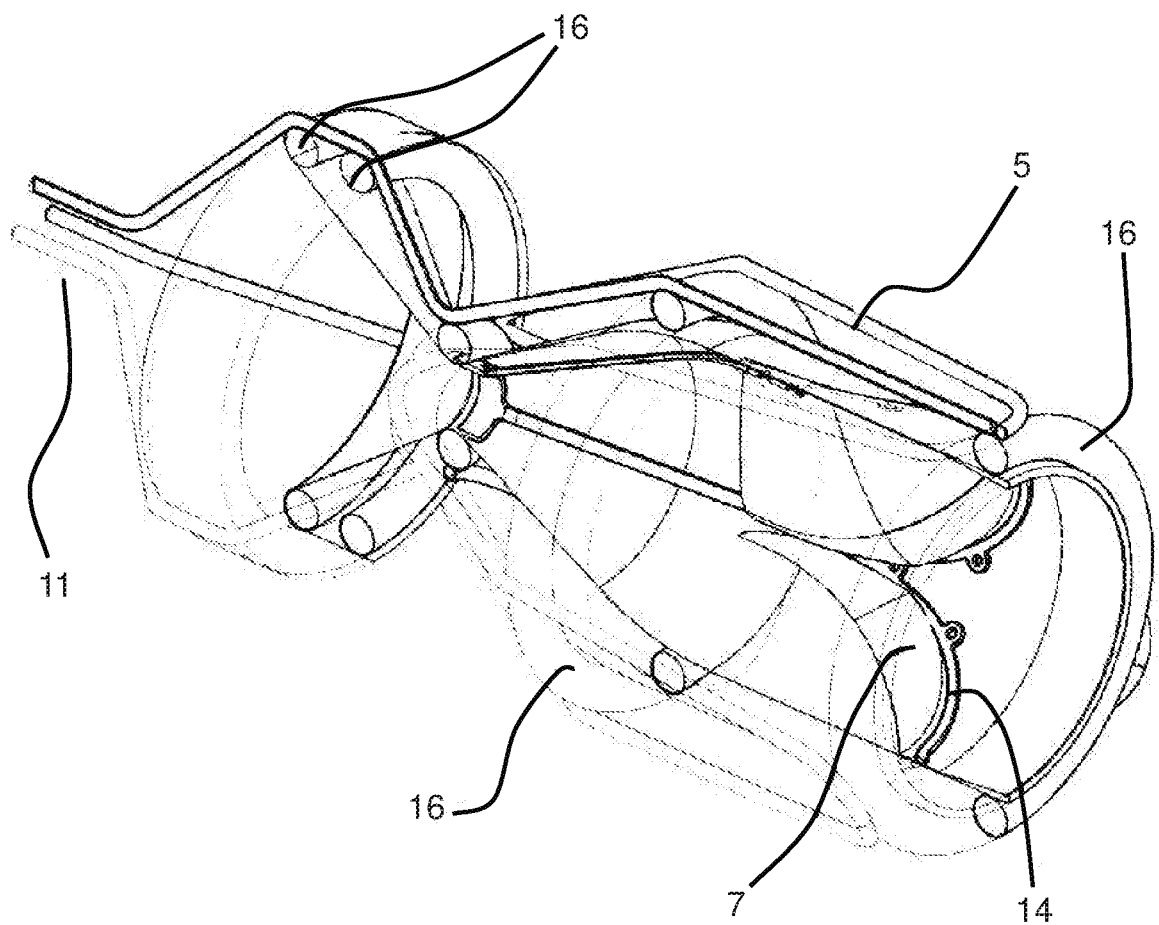
FIG. 20: the device 4 as described in FIG. 19. The internal structure is visible. The valve's support stent 14 is visible.

In FIGS. 19 to 20 a specific embodiment of an inflatable device is described.

The use of inflatable structures has the aim to minimize the number of different materials involved in the manufacturing and it allows a reduced encumbrance of the collapsed device. Moreover it allows an easy positioning of the device thanks to the radiopaque characteristics of the $CO_2$ filler.

Several different embodiments can apply to the inflatable group, starting from a device 4 with all inflated support structures, with conveyor 6 inside the external support structure 5 and the prosthetic valve 15 directly joined to it and ending to a device 4 with longitudinal elements of the external support structure 5 and valve's support stent 14 made of self-expanding materials, such as nitinol, and conveyor external to the structure 5.

As far as concerns the opening mechanism for the valve, which is intended to be used at the end of the restoring procedure to verify the relevant outcomes on the diseased valve, different embodiments can apply, acting directly on the leaflets 7 and/or on the valve's support stent 14 by means of shaft mechanisms, either pushing/pulling or rotating, proximally holded inside the internal catheter 3' and commanded by the delivery system.

The invention claimed is:

1. A transcatheter temporary valve prosthesis for a blood vessel, the prosthesis comprising:
   an expandable support structure having a distal and a proximal end;
   a valve located at the distal end;
   a filter; and
   a conveyor including a funnel portion located at the proximal end and a tubular part located at the distal end, the funnel portion and the tubular part being integrally formed, a narrow part of the funnel portion being connected to the tubular part, wherein the expandable support structure is separate from the conveyor and has a tubular shape when expanded, and wherein the funnel portion of the conveyor, the tubular part of the conveyor, and the valve are interconnected and extend within the expandable support structure from the proximal end to the distal end and include a central passage configured to introduce other devices to the transcatheter temporary valve prosthesis.

2. The prosthesis according to claim 1, wherein the filter and the conveyor are combined to form a single element.

3. The prosthesis according to claim 1, wherein the filter is disposed against an inner wall of the support structure.

4. The prosthesis according to claim 3, wherein the distal end of the conveyor includes a bi-directional normally closed valve that is configured to be crossed on demand to perform as a leak-free introducer for other devices.

5. The prosthesis according to claim 1, wherein the valve includes a plurality of leaflets.

6. The transcatheter temporary valve prosthesis of claim 5, wherein, in a closed position, a coaptation of the several leaflets of the valve adhere to an outer surface of the tubular part.

7. The prosthesis according to claim 1, wherein the prosthesis is configured to be deployed and positioned in an anatomic operating site to support blood circulation in case of acute significant valve insufficiency.

8. The prosthesis according to claim 1, wherein the prosthesis is configured to support the blood circulation in case of acute significant aortic valve insufficiency.

9. The prosthesis according to claim 1, further comprising:

an epiaortic vessel deflector configured for placement along the epiaortic vessels to prevent debris embolizing into the epiaortic vessels.

10. The prosthesis according to claim 1, further comprising:

two coronary artery deflectors configured for placement in front of the coronary ostia, preventing debris embolization into the coronary arteries.

11. The prosthesis according to claim 1, wherein the valve, the filter, and the conveyor are located within the support structure.

12. The prosthesis according to claim 1, wherein the support structure has a conical termination comprising a plurality of tethering struts that are configured to join an internal catheter, and wherein the support structure is collapsible from an expanded state into a compressed state by pulling on the tethering struts.

13. The transcatheter temporary valve prosthesis of claim 1, wherein the valve is disposed in an area between the tubular part and the expandable support structure.

14. The transcatheter temporary valve prosthesis of claim 1, wherein a wide opening of the funnel portion of the conveyor opens towards the proximal end.

15. The transcatheter temporary valve prosthesis of claim 1, further comprising:

tethering struts arranged to connect the expandable support structure to an internal shaft catheter, one end of the tethering struts arranged at a wide part of the funnel portion.

16. The transcatheter temporary valve prosthesis of claim 1, wherein a wide part of the funnel portion is arranged to extend circumferentially to an entire width of the expandable support structure.

* * * * *